United States Patent
Chilkoti et al.

(10) Patent No.: US 11,130,987 B2
(45) Date of Patent: Sep. 28, 2021

(54) DIRECT DETECTION OF RNA BY SURFACE INITIATED ENZYMATIC POLYMERIZATION

(71) Applicant: SENTILUS HOLDCO, LLC, Norcross, GA (US)

(72) Inventors: Ashutosh Chilkoti, Durham, NC (US); Srinath Rangarajan, Seattle, WA (US); Miriam Amiram, Stamford, CT (US); Angus Hucknall, Durham, NC (US)

(73) Assignee: SENTILUS HOLDCO, LLC, Norcross, GA (US)

( * ) Notice: Subject to any disclaimer, the term of this patent is extended or adjusted under 35 U.S.C. 154(b) by 614 days.

(21) Appl. No.: 15/039,995

(22) PCT Filed: Nov. 25, 2014

(86) PCT No.: PCT/US2014/067376
§ 371 (c)(1),
(2) Date: May 27, 2016

(87) PCT Pub. No.: WO2015/081088
PCT Pub. Date: Jun. 4, 2015

(65) Prior Publication Data
US 2017/0058329 A1 Mar. 2, 2017

Related U.S. Application Data

(60) Provisional application No. 61/909,958, filed on Nov. 27, 2013.

(51) Int. Cl.
*C12P 19/34* (2006.01)
*C12Q 1/6816* (2018.01)
(Continued)

(52) U.S. Cl.
CPC ......... *C12Q 1/6816* (2013.01); *C12Q 1/6883* (2013.01); *C12Q 1/6886* (2013.01);
(Continued)

(58) Field of Classification Search
USPC ......... 435/6.1, 6.11, 6.12, 91.1, 91.2, 91.51; 436/94, 501; 536/23.1, 24.3, 24.33, 25.3
See application file for complete search history.

(56) References Cited

U.S. PATENT DOCUMENTS

| 7,713,689 B2 | 5/2010 | Chilkoti |
| 8,367,314 B2 | 2/2013 | Chilkoti |

(Continued)

FOREIGN PATENT DOCUMENTS

| WO | WO 2004057016 A2 | 7/2004 |
| WO | WO 2011049964 A1 | 4/2011 |
| WO | WO-2015/081088 A1 | 6/2015 |

OTHER PUBLICATIONS

Poly(A) Polymerase Tailing Kit from epibio.com. Printed on Aug. 30, 2019.*

(Continued)

*Primary Examiner* — Frank W Lu
(74) *Attorney, Agent, or Firm* — Mintz Levin; Todd B. Buck

(57) ABSTRACT

Disclosed herein are methods of detecting a target RNA, methods of diagnosing an individual with a disease or condition when a target RNA associated with the disease or condition is detected, and methods of conveying via a communication medium data from the detection of a target RNA.

44 Claims, 18 Drawing Sheets

Specification includes a Sequence Listing.

(51) Int. Cl.
*C12Q 1/6883* (2018.01)
*C12Q 1/6886* (2018.01)
*G01N 21/64* (2006.01)

(52) U.S. Cl.
CPC .......... *C12Q 2600/158* (2013.01); *G01N 2021/6439* (2013.01)

(56) References Cited

U.S. PATENT DOCUMENTS

| | | | |
|---|---|---|---|
| 8,796,184 | B2 | 8/2014 | Chilkoti et al. |
| 2004/0067492 | A1* | 4/2004 | Peng .............. C12Q 1/6837 435/6.13 |
| 2006/0057180 | A1 | 3/2006 | Chilkoti et al. |
| 2013/0059736 | A1 | 3/2013 | Galas et al. |

OTHER PUBLICATIONS

Jinhua Dai et al., "High-Capacity Binding of Proteins by Poly(Acrylic Acid) Brushes and Their Derivatives", Langmuir, vol. 22, pp. 4274-4281 (2006).

Chow et al. (2005) "Enzymatic fabrication of DNA nanostructures: Extension of a self-assembled oligonucleotide monolayer on gold arrays," Journal of the American Chemical Society. 127(41):14122-14123.

Chow et al. (2007) "Surface-initiated enzymatic polymerization of DNA," Langmuir. 23(23):11712-11717.

Hucknall et al. (2009) "In pursuit of zero: polymer brushes that resist the adsorption of proteins," Advanced Materials. 21(23):2441-2446.

Hucknall et al. (2009) "Simple fabrication of antibody microarrays on nonfouling polymer brushes with femtomolar sensitivity for protein analytes in serum and blood," Advanced Materials. 21(19):1968-1971.

Tjong et al. (2011) "Amplified on-chip fluorescence detection of DNA hybridization by surface-initiated enzymatic polymerization," Analytical Chemistry. 83(13):5153-5159.

Tjong et al. (2012) "Direct fluorescence detection of RNA on microarrays by surface-initiated enzymatic polymerization," Analytical Chemistry. 85(1):426-433.

Wan et al. (2012) "A surface-initiated enzymatic polymerization strategy for electrochemical DNA sensors," Biosensors and Bioelectronics. 41:526-531.

International Search Report with Written Opinion corresponding to International Patent Application No. PCT/US2014/067376, dated Feb. 9, 2015, 15 pages.

International Preliminary Report on Patentability corresponding to International Patent Application No. PCT/US2014/067376, dated May 31, 2016, 12 pages.

* cited by examiner

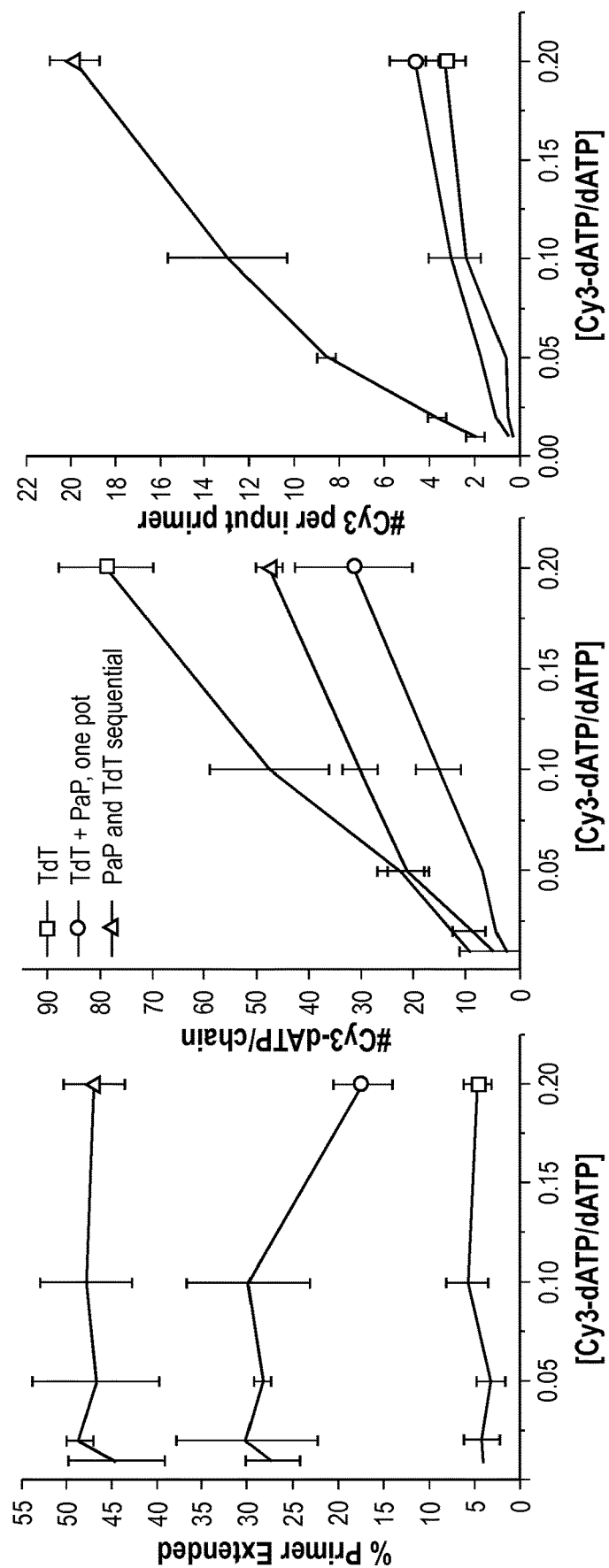

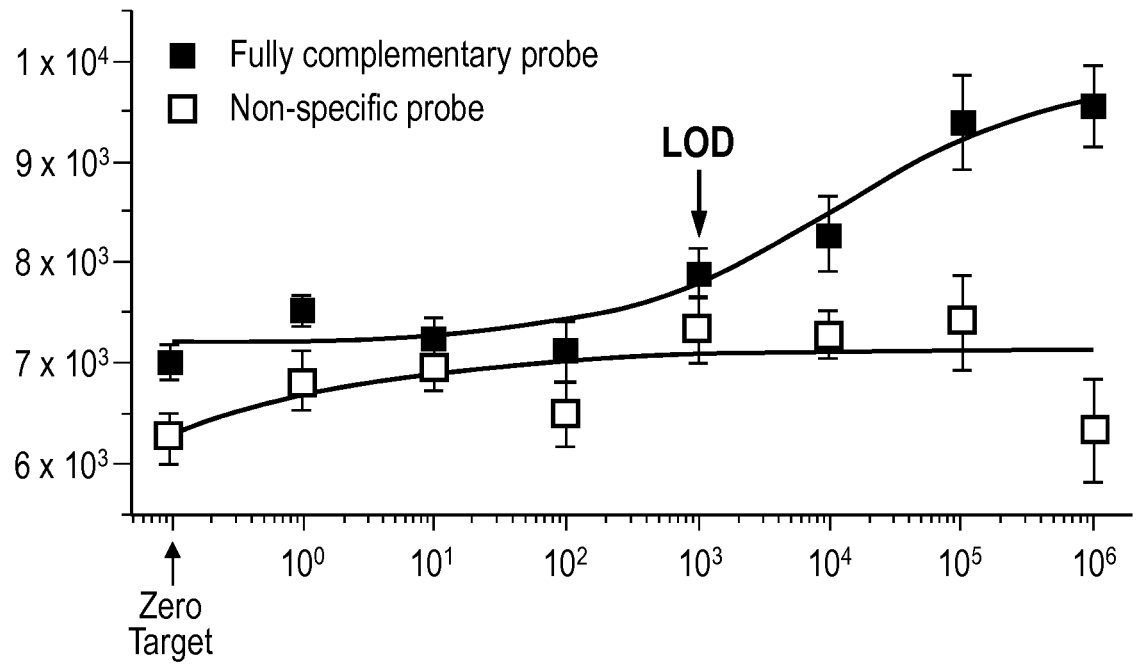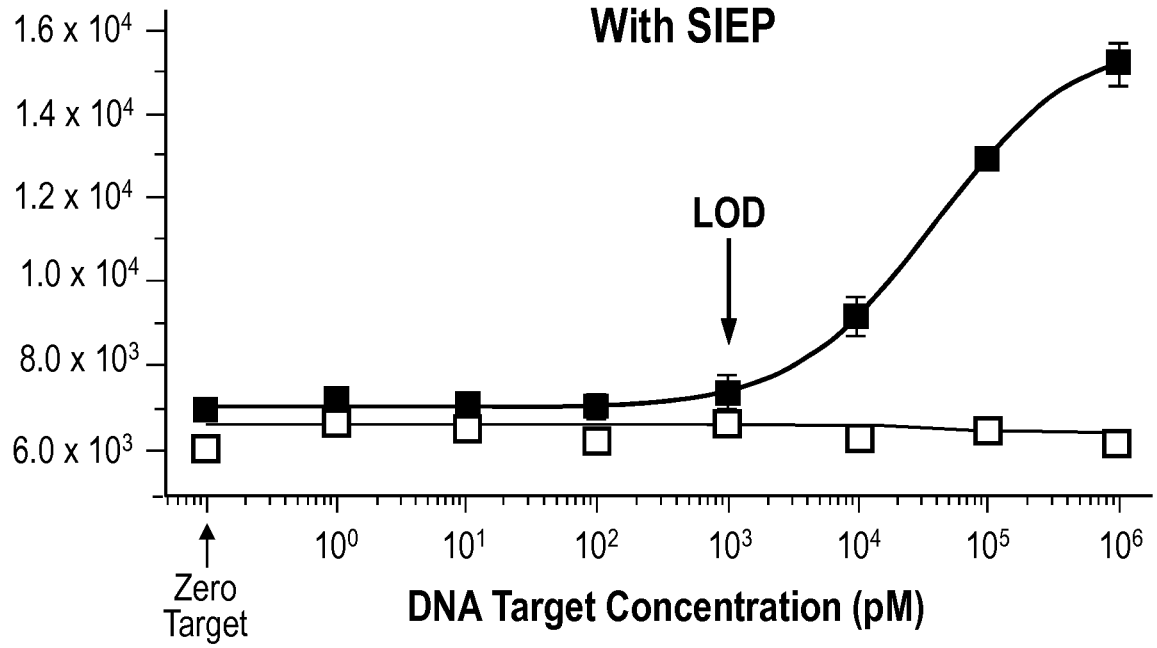
Fig. 8(b)

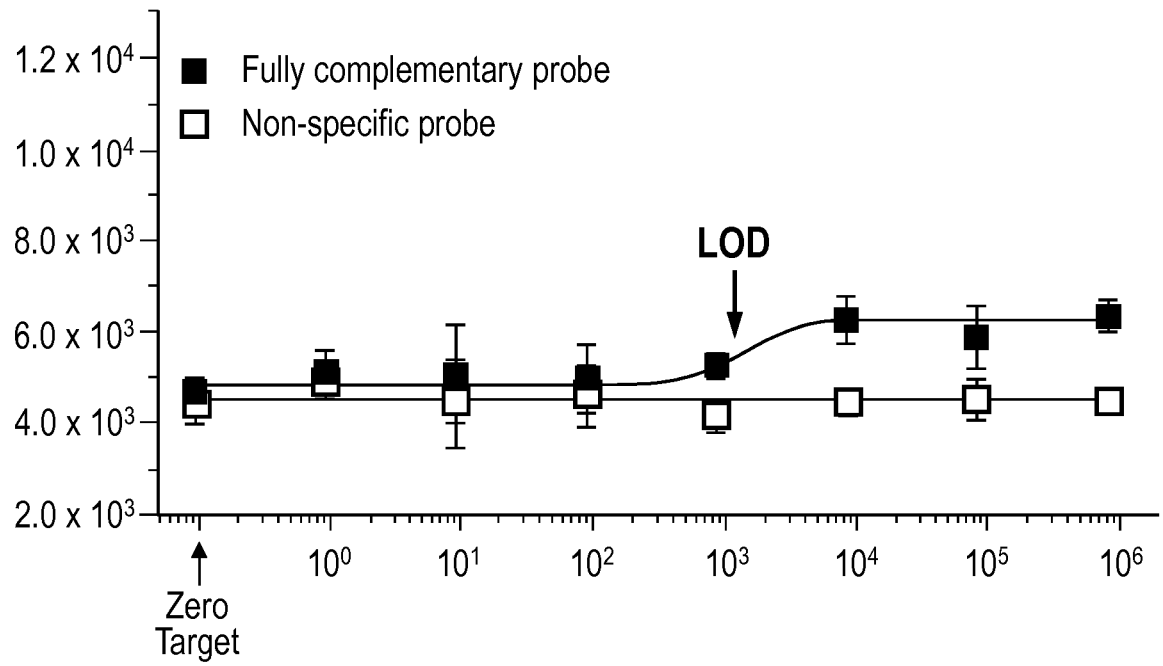
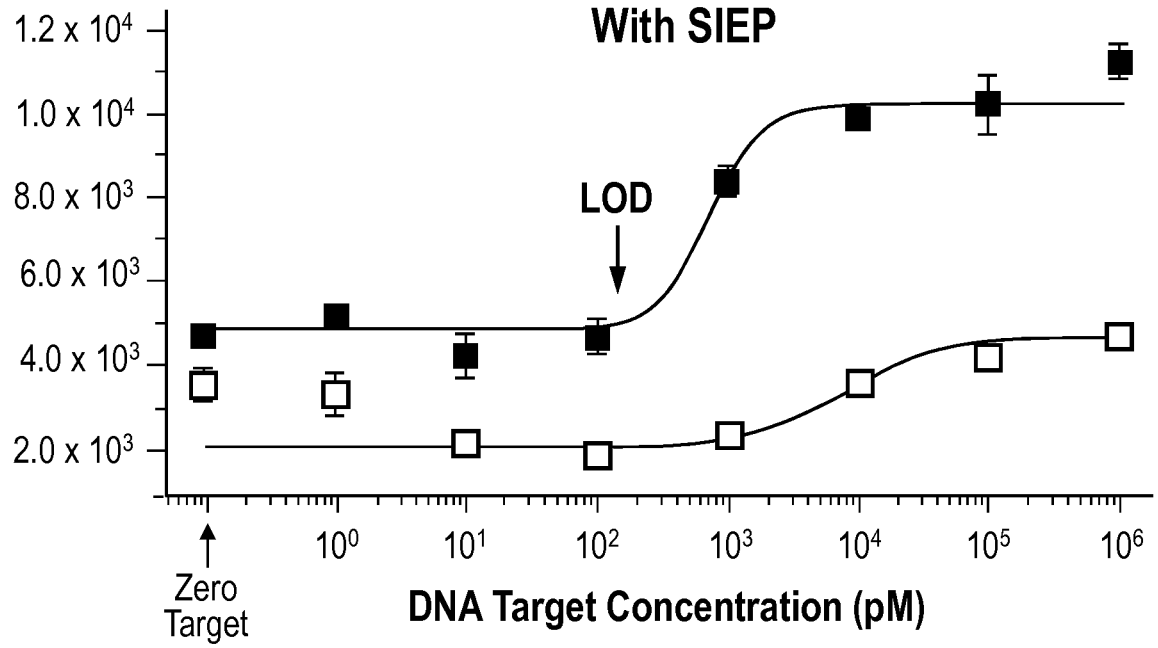
Fig. 9(b)

SEQUENCE LISTING

```
<160> NUMBER OF SEQ ID NOS: 12

<210> SEQ ID NO 1
<211> LENGTH: 17
<212> TYPE: DNA
<213> ORGANISM: Artificial Sequence
<220> FEATURE:
```

<223> OTHER INFORMATION: DNA in 5'-biotinylated 17-mer PNA probe

<400> SEQUENCE: 1
gtccaccacc ctgttgc                                                17

<210> SEQ ID NO 2
<211> LENGTH: 17
<212> TYPE: DNA
<213> ORGANISM: Artificial Sequence
<220> FEATURE:
<223> OTHER INFORMATION: DNA in non-specific probe from HBV sequence

<400> SEQUENCE: 2
accttgtcat gtaccat                                                17

<210> SEQ ID NO 3
<211> LENGTH: 42
<212> TYPE: RNA
<213> ORGANISM: Artificial Sequence
<220> FEATURE:
<223> OTHER INFORMATION: Synthetic RNA target

<400> SEQUENCE: 3
rgrcrararc rargrgrgru rgrgrurgrg rarcrcrurc ra                     42

<210> SEQ ID NO 4
<211> LENGTH: 17
<212> TYPE: DNA
<213> ORGANISM: Artificial Sequence
<220> FEATURE:
<223> OTHER INFORMATION: DNA in PNA probe for GADPH and PRSS21

<400> SEQUENCE: 4
cttcggtgac tcaggtg                                                17

<210> SEQ ID NO 5
<211> LENGTH: 17
<212> TYPE: DNA
<213> ORGANISM: Artificial Sequence
<220> FEATURE:
<223> OTHER INFORMATION: DNA in PNA probe for IFI44

<400> SEQUENCE: 5
ctgagacgaa tgctatg                                                17

<210> SEQ ID NO 6
<211> LENGTH: 34
<212> TYPE: RNA
<213> ORGANISM: Artificial Sequence
<220> FEATURE:
<223> OTHER INFORMATION: RNA primer (initiator)

<400> SEQUENCE: 6
rgrcrararc rargrgrgru rgrgrurgrg rarc                             34

<210> SEQ ID NO 7
<211> LENGTH: 15
<212> TYPE: DNA
<213> ORGANISM: Artificial Sequence
<220> FEATURE:
<223> OTHER INFORMATION: DNA in DNA primer

<400> SEQUENCE: 7
cgggcaacat acctt                                                  15

```
<210> SEQ ID NO 8
<211> LENGTH: 15
<212> TYPE: DNA
<213> ORGANISM: Artificial Sequence
<220> FEATURE:
<223> OTHER INFORMATION: DNA in PNA primer

<400> SEQUENCE: 8
cgggcaacat acctt                                                        15

<210> SEQ ID NO 9
<211> LENGTH: 17
<212> TYPE: DNA
<213> ORGANISM: Artificial Sequence
<220> FEATURE:
<223> OTHER INFORMATION: DNA in fully complementary PNA probe

<400> SEQUENCE: 9
caatgccagc cccagcg                                                      17

<210> SEQ ID NO 10
<211> LENGTH: 17
<212> TYPE: DNA
<213> ORGANISM: Artificial Sequence
<220> FEATURE:
<223> OTHER INFORMATION: DNA in non-specific PNA probe

<400> SEQUENCE: 10
gttgctggta gtttatg                                                      17

<210> SEQ ID NO 11
<211> LENGTH: 22
<212> TYPE: DNA
<213> ORGANISM: Artificial Sequence
<220> FEATURE:
<223> OTHER INFORMATION: Hybridized target

<400> SEQUENCE: 11
cgctggggct ggcattgccc tc                                                22

<210> SEQ ID NO 12
<211> LENGTH: 27
<212> TYPE: RNA
<213> ORGANISM: Artificial Sequence
<220> FEATURE:
<223> OTHER INFORMATION: Target RNA

<400> SEQUENCE: 12
uuugacgcug gggcuggcau ugcccuc                                           27
```

DIRECT DETECTION OF RNA BY SURFACE INITIATED ENZYMATIC POLYMERIZATION

CROSS-REFERENCE TO RELATED APPLICATIONS

This application is the U.S. National Stage of International Application PCT/US2014/067376 filed Nov. 25, 2014, published as WO/2015/081088 on Jun. 4, 2015, which claims priority to U.S. Provisional Patent Application No. 61/909,958 filed Nov. 27, 2013, each of which is incorporated by reference herein in its entirety.

INCORPORATION BY REFERENCE OF SEQUENCE LISTING

This application contains references to amino acids and/or nucleic acid sequences that have been filed herewith on Nov. 9, 2016 as a sequence listing text file. The aforementioned sequence listing is hereby incorporated by reference in its entirety pursuant to 37 C.F.R. § 1.52(e)(5).

TECHNICAL FIELD

Described herein are methods of detecting a target RNA and methods of diagnosing an individual with a disease or condition when a target RNA associated with the disease or condition is detected, and methods of conveying via a communication medium data from the detection of a target RNA.

BACKGROUND

Microarray technology is a powerful method for RNA quantification that is capable of analyzing thousands of genes in parallel, and has been used to investigate differential gene expression, detect pathogens, and more recently has been used for the quantification of microRNA (miRNA) levels. Although they are sensitive, many of these techniques require converting the target RNA molecules to complementary DNA (cDNA), a molecule that is less susceptible to degradation, through a reverse transcription step, followed by an optional linear (in vitro transcription-based) or exponential (PCR-based, e.g., polymerase chain reaction based) amplification of the original target and subsequent detection. Reverse transcription and target amplification is often accompanied by enzymatic or chemical labeling of cDNA molecules for detection.

This approach has several potential limitations. First, it requires multiple steps that are time consuming, labor intensive, and involve extensive sample manipulation, which has the potential to introduce errors in the original mRNA concentration due to loss of material and the introduction of systematic bias. Second, the direct incorporation of labels into cDNA molecules can reduce their hybridization efficiency, further confounding analysis. Finally, because samples are labeled indiscriminately, even samples that do not hybridize can generate a false positive or background signal because of non-specific binding of unhybridized target molecules to the surface.

Therefore timely, accurate, and sensitive methods for detecting biomarkers associated with diseases or conditions are desirable, especially in a clinical setting. RNAs can be biomarkers of diseases or conditions. Detection of target RNAs (e.g., biomarkers) can indicate the presence of the disease or condition. Detection of RNA's typically requires e.g., reverse RNA transcription to DNA, amplification (e.g., linear and/or exponential amplification) of the transcribed DNA molecule, and sequencing of the amplified DNA. The ability to detect target RNAs, e.g., associated with a disease or condition from e.g., a biological sample, in a timely, robust, sensitive, and accurate manner, without the need for: transcription of the target RNA to DNA, amplification of the resulting DNA, and sequencing of the resulting amplified DNA, is a desirable but unmet need. This need and others are addressed by the inventive embodiments recited herein.

SUMMARY

Herein, we report the use of surface initiated enzymatic polymerization (SIEP) for detection of RNA in a microarray format. This method can incorporate multiple fluorophores into a RNA strand using the sequential and complementary reactions catalyzed by e.g. yeast poly(A) polymerase (PaP) to incorporate deoxyadenosine triphosphate (dATP) at the 3'-OH of a target RNA molecule, followed by e.g., terminal deoxynucleotidyl transferase (TdT) to catalyze the sequential addition of a mixture of natural and fluorescent deoxynucleotides (dNTPs) at the 3'-OH of a RNA-DNA hybrid (e.g., an extended RNA-DNA hybrid). In some embodiments described herein, the 3'-end of RNA can be efficiently converted into DNA (~50% conversion) by polymerization of dATP using yeast PaP, and the short DNA strand appended to the end of the RNA by PaP acts as the initiator for the TdT catalyzed polymerization of longer DNA strands from a mixture of natural and fluorescently labeled dNTPs that contains up to ~45 Cy3 fluorophores per 1 Kb DNA. In some aspects, the methods described herein provide an approximate 2 pM limit of detection (LOD) and a 3-log linear dynamic range for hybridization of a short 21 base long RNA target to an immobilized peptide nucleic acid probe, while fragmented mRNA targets from four different full length mRNA transcripts may yield a ~10 pM LOD with a similar dynamic range in a microarray format.

Further provided herein is a support comprising a polynucleotide probe annealed to a RNA-DNA hybrid, or an extended RNA-DNA hybrid, a target RNA.

In some embodiments described herein is a method of detecting a target RNA, comprising the steps of: a) annealing a target RNA to a polynucleotide probe; b) extending the annealed target RNA with at least one deoxyribonucleotide triphosphate to form an RNA-DNA hybrid c) extending the RNA-DNA hybrid with at least one deoxyribonucleotide triphosphate to form an extended RNA-DNA hybrid; and d) detecting the presence of the target RNA by detecting the presence of the extended RNA-DNA hybrid. In one aspect, in step b) the 3' end of the target RNA is extended. In another aspect, steps b) and c) are conducted sequentially. In another aspect, steps b) and c) are conducted together. Another aspect further comprises, between steps c) and d), washing the solid support. Another aspect further comprises, between steps a) and b), washing the solid support. Another aspect further comprises before step a) printing the polynucleotide probe on a support. Another aspect further comprises associating the annealed polynucleotide probe—target RNA from step a) with a support. Another aspect further comprises associating the annealed DNA-RNA hybrid from step b) with a solid support. Another aspect further comprises associating the annealed extended DNA-RNA hybrid from step c) with a solid support. In another aspect, the at least one deoxyribonucleotide triphosphate is deoxyadenosine triphosphate. Another aspect further comprises, before step a) printing the polynucleotide probe onto the solid support. In another aspect, the target RNA is not labeled before step b). In another aspect, the target RNA is not labeled before step c). In another aspect, the extending in step b) is conducted isothermally. In another aspect, the extending in step c) is conducted isothermally. In another aspect, at least one of steps a), b), c), and/or d) is conducted isothermally. In some aspects, annealing is conducted at about 42° C. In another aspect, wherein in step b) an RNA that is not annealed to the polynucleotide probe is not extended by a deoxyribonucleotide triphosphate.

In some of the embodiments, the number of deoxyribonucleotides added to the target RNA to form an RNA-DNA hybrid ranges from 1 to about 20, from 1 to about 15, from 1 to about 10, from 1 to about 5, from 1 to about 3, from 1 to about 2, about 1, about 2, about 3, about 4, about 5, about 6, about 7, about 8, about 9, about 10, about 15, or about 20. In another aspect, in step c), the number of deoxyribonucleotides added to the RNA-DNA hybrid ranges from 1 to about 1,000, about 1 to 500, about 1 to 150, about 1 to 100, about 1 to 90, about 1 to 70, about 1 to 50, about 1 to 40, about 1 to 30, about 1 to 20, about 1 to 10, about 1 to 5, about 5, about 10, about 15, about 20, about 25, about 30, about 35, about 40, about 45, about 50, about 60, about 70, about 80, about 90, about 100, about 200, about 300, about 400, about 500, or about 1000. In another aspect, at least 1%, at least 10%, at least 20%, at least 30%, at least 40%, at least 50%, at least 60%, at least 70%, at least 80%, at least 90% at least 95%, about 1%, about 10%, about 20%, about 30%, about 40%, about 50%, about 60%, about 70%, about 80%, about 90%, about 95%, or about 100% of the deoxyribonucleotides added to the RNA-DNA hybrid are labeled.

In some aspects, the extended RNA-DNA probe may be detected visually. In some aspects, the at least one deoxyribonucleotide triphosphate for extending the RNA-DNA hybrid may be labeled. In some aspects, the labeled deoxyribonucleotide triphosphate is labeled with a fluorescent label. In some aspects, the labeled deoxyribonucleotide triphosphate is labeled with a radio label. In some aspects, the labeled deoxyribonucleotide triphosphate is labeled with a chromophore.

In one embodiment, the detecting the extended RNA-DNA hybrid comprises fluorescence detection methods. In one aspect, determining the amount of target RNA present is based on a fluorescent standard.

In another embodiment, the detecting the extended RNA-DNA hybrid comprises radioactivity detection methods. In one aspect, determining the amount of target RNA present may is based on a radiolabel standard.

In another the embodiment, the detecting the extended RNA-DNA hybrid comprises electrochemical detection methods.

In some of the embodiments, the detecting the extended RNA-DNA hybrid may be conducted with a microscope. In some aspects, the microscope comprises an atomic force microscope In some of the embodiments, before detecting the presence of the extended RNA-DNA hybrid, the extended RNA-DNA hybrid is contacted with positively charged metal nano-particles. In some aspects, the positively charged nano-particles are selected from the group consisting of positively charged gold nano-particles, positively charged silver-nano particles, and combinations thereof.

In some of the embodiments, detecting the extended RNA-DNA hybrid comprises visually detecting a complex comprising the extended RNA-DNA hybrid and the positively charged metal nano-particles. In some aspects, visually detecting the metal nanoparticle and extended RNA-DNA hybrid complex is conducted by a microscope. In some aspects, the metal nano-particles have a size range of less than 1000 nm, less than 500 nm, less than 100 nm, less than 50 nm, less than 10 nm, less than 1 nm, about 1000 nm, about 500 nm, about 100 nm, about 50 nm, about 10 nm, about 1 nm, about 0.05 nm, or about 0.001 nm. In some aspects, the positively charged metal particles are spherical.

In some of the embodiments, the detecting the extended RNA-DNA hybrid is conducted by detecting a change of mass.

In some of the embodiments, the target RNA is a viral RNA, a bacterial RNA, a plant RNA, a mammalian RNA, a yeast RNA, a fungus RNA, a prokaryotic RNA, a eukaryotic RNA, an archae RNA, a human RNA, a synthetic RNA, a synthetic non-natural RNA, or a fragment of one of these. In some aspects, the target RNA is an mRNA, a tRNA, an rRNA, a siRNA, a miRNA, or a fragment of one of these. In some aspects, the target RNA is associated with a disease or condition selected from the group consisting of: human immunodeficiency virus (HIV), herpes simplex virus (HSV), herpes simplex virus-1 (HSV-1), herpes simplex virus-2 (HSV-2), human papillomavirus (HPV), human papillomavirus-16 (HPV-16), human papillomavirus-18 (HPV-18), hepatitis C virus (HCV), hepatitis B virus (HBV), hepatitis A virus (HVA), cytomegalovirus, tuberculosis, *Chlamydia*, gonorrhea, syphilis, Methicillin-resistant *Staphylococcus aureus* (MRSA), mumps, measles, cholera, typhoid fever, rheumatic fever, cancer, stroke, ischemic disease, cardiovascular disease, Lyme disease, rabies, influenza, Ebola, pregnancy, a fungal infection, a bacterial infection, polio, small pox, diabetes, diabetes type I, diabetes type II, a viral infection, an autoimmune disease, and any combination thereof.

In any of the embodiments, the target RNA may comprise a number of ribonucleotides that can be at least 5, at least 10, at least 20, at least 50, at least 100, at least 500, at least 1000, at least 10,000, at least 50,000, from 1 to 10, from 1 to 100, from 1 to 1000, from 1 to 10,000, about 10, about 20, about 30, about 40, about 50, about 100, about 500, about 1000, about 10,000, or about 100,000.

In some of the embodiments, the methods described herein do not comprise reverse transcribing RNA to DNA.

In some other embodiments, the methods described herein do not comprise amplifying DNA.

In some other embodiments, the methods described herein do not comprise employing polymerase chain reaction (PCR).

In some other embodiments, the methods described herein do not comprise sequencing DNA.

In some other embodiments, the target RNA, prior to hybridization, is not labeled.

In some of the embodiments, the RNA-DNA is extended with a polymerase. In some aspects, the polymerase is a poly (A) polymerase. In some aspects, the poly (A) polymerase is a yeast poly (A) polymerase (e.g., PaP).

In some of the embodiments, the RNA-DNA is extended with a DNA polymerase. In some aspects, the DNA polymerase is a terminal deoxynucleotidyl transferase (e.g., TdT). In some aspects, the DNA polymerase is a template independent DNA-polymerase. In some aspects, the DNA polymerase recognizes an extended 3' OH end of an RNA-DNA hybrid.

In some of the embodiments, the polynucleotide probe comprises RNA. In some of the embodiments, the polynucleotide probe comprises DNA. In some aspects, the polynucleotide probe blocked with a blocking group at its 5' end. In some aspects, the blocking group is an acyl group.

In some aspects, the blocking group is an acetyl group. In some aspects, the polynucleotide probe comprises a number of polynucleotides that can be at least 5, at least 10, at least 20, at least 50, at least 100, at least 500, at least 1000, at least 10,000, at least 50,000, from 1 to 10, from 1 to 100, from 1 to 1000, from 1 to 10,000, about 10, about 20, about 30, about 40, about 50, about 100, about 500, about 1000, about 10,000, or about 100,000. In some aspects, the polynucleotide probe is selective for the target RNA.

In some of the embodiments, the polynucleotide probe is covalently attached to a tether. In some aspects, the tether is a protein. In some aspects, the tether is biotin, a his tag, a flag tag, an AviTag, a calmodulin tag, an HA tag, a Myc-tag, an S-tag, a SBP tag, a softag 1, a softag 3, a V5 tag, an Xpress tag, an isopep tag, a spy tag, BCCP, a glutathione-S-transferase tag, a green fluorescent protein tag, a maltose binding protein tag, a nus tag, a strep tag, a thioredoxin tag, a TC tag, or a Ty tag. In some aspects, the tether is biotin. In some aspects, the tether is associated with an anchor. In some aspects, the association between the tether and anchor is non-covalent or covalent. In some aspects, the anchor is associated with a solid support or a layer or a surface thereof. In some aspects, the anchor is a protein. In some aspects, the anchor is an antibody or a fragment thereof. In some aspects, the anchor comprises a nickel or cobalt chelate. In some aspects, the tether comprises biotin and the anchor protein comprises streptavidin. In some aspects, the anchor comprises streptavidin, calmodulin, an anion-exchange resin, an antibody, a fragment thereof, a nickel chelate, cobalt chelate, pilin-C protein, SypCatcher protein, glutathione S transferase, amylose agarose, or any combination thereof.

In some of the embodiments, the polynucleotide probe further comprises a spacer covalently attached between the polynucleotide probe and the tether. In some aspects, the spacer is an amino acid. In some aspects, the amino acid comprises lysine. In some aspects, the amino acid is histidine, isoleucine, leucine, lysine, methionine, phenylalanine, threonine, tryptophan, valine, alanine, arginine asparagine, aspartic acid, cysteine, glutamic acid, glutamine, glycine, ornithine, proline, selenocystein, serine, or tyrosine.

In some of the embodiments, the polynucleotide probe is directly associated with a solid support or a layer or surface thereof. In some aspects, the association with a solid support or a layer or surface thereof is non-covalent or covalent. In some aspects, the polynucleotide probe is non-covalently associated with the solid support or a layer or a surface thereof. In some aspects, the polynucleotide probe is non-covalently associated with a non-fouling, bottle-brush polymer layer associated with the solid support. In some aspects, the polynucleotide probe is covalently associated with a non-fouling, bottle-brush polymer layer associated with the solid support.

Any of the embodiments described herein may further comprise a solid support, comprising: a) a substrate; b) optionally, a linking layer; and c) a non-fouling, bottle-brush polymer layer, wherein the optional linking layer is between the substrate and the non-fouling, bottle-brush polymer layer.

In some of the embodiments, the polynucleotide probe comprises DNA.

In some of the embodiments, the polynucleotide probe comprises a peptide nucleic acid (PNA) probe.

Some of the embodiments described herein further comprise, dephosphorylating the annealed target RNA. In some aspects, dephosphorylating the annealed target RNA is conducted with a base. In some aspects, the base is an organic or inorganic hydroxide, for example, ammonium hydroxide, lithium hydroxide, potassium hydroxide, sodium hydroxide, magnesium hydroxide, cesium hydroxide, calcium hydroxide, and any combination thereof. In some aspects, the dephosphorylating is conducted with an enzyme. In some aspects, the enzyme is a phosphatase.

In some of the embodiments, the polynucleotide probe is associated with a support. In some aspects, the support is a solid support.

In any of the embodiments described herein the target RNA can be associated with a disease or condition, and the methods described herein further comprise diagnosing the disease or condition in a patient, who can be a human, when the target RNA is detected. In some aspects, the methods described herein comprise a control that does not detect the target RNA.

In some of the embodiments described herein, the lower limit of detection of the target RNA is greater than or equal to 50 fM, greater than or equal to 100 fM, greater than or equal to 1000 fM, greater than or equal to 10,000 fM, greater than or equal to 100,000 fM, greater than or equal to 1,000,000 fM, about 50 fM, about 100 fM, about 500 fM, about 1000 fM, about 5,000 fM, about 10,000 fM, about 50,000 fM, about 100,000 fM, or about 1,000,000 fM.

In some of the embodiments described herein, the methods described herein provide for the detection of multiple target RNAs simultaneously.

In some of the embodiments described herein, the method is conducted using an array of polynucleotide probes. In some aspects, the array is a microarray. In some aspects, the array comprises at least 5, at least 10, at least 15, at least 20, at least 25, at least 30, at least 40, at least 50, at least 100, at least 500, at least 1000, at least 10,000, at least 50,000, about 1, about 5, about 10, about 50, about 100, about 1000, about 5000, about 10,000, about 50,000, or about 100,000 polynucleotide probes.

In some of the embodiments described herein, the methods further comprise capturing data, wherein the data can comprise an image comprising the extended DNA-RNA hybrid. In some aspects, the capturing is a recording, such as a digital recording. In some aspects, the methods described herein further comprise transmitting via a communication medium the captured data. In some aspects, the transmitting a result via a communication medium is conducted after detecting the presence of the target RNA by detecting the presence of the extended RNA-DNA hybrid by the methods described herein.

In some of the embodiments, the target RNA is derived from a biological sample. In some aspects, the biological sample is subjected to lysing conditions prior to annealing a target RNA to a polynucleotide probe;

In some of the embodiments described herein, the methods described herein comprise at least two different polynucleotide probes that bind to at least two different target RNAs.

In any of the embodiments described herein, the non-fouling, bottle brush layer may comprise poly(oligo(ethylene glycol) methacrylate (e.g., pOEGMA).

In some of the embodiments described herein, the solid support is a medical device or a portion thereof.

In any of the embodiments described herein, the bottle brush polymer layer can be a copolymer.

In any of the embodiments described herein the bottle brush polymer layer can be covalently connected to the linking layer.

In any of the embodiments described herein the linking layer can be a polymer or a copolymer.

In any of the embodiments described herein, the target RNA, when annealed to the polynucleotide probe, can contain an overhanging 3' end that is not annealed to the polynucleotide probe.

In any of the embodiments described herein, the determining, the diagnosing, or the determining and the diagnosing can be computer implemented.

In any of the embodiments described herein, the methods described herein may further comprise treating a subject who contains a detected target RNA associated with a disease or condition.

INCORPORATION BY REFERENCE

All publications, patents, and patent applications mentioned in this specification are incorporated by reference, in their entireties, unless otherwise noted and limited to a specific teaching of a technique, reagent, or method thereof. In the event of a conflict between a term herein and a term incorporated by reference, the terms herein controls.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 3(a), 3(b), and 3(c), show quantification of incorporated, Cy3-labeled nucleotides into an RNA.

FIG. 8(b) shows dose response curves of hybridized 22-mer DNA target on a PNA probe, with and without SIEP simplification.

FIG. 9(b) shows dose response curves of hybridized 28-mer RNA target on PNA probe, with and without SIEP amplification. A sensitivity of 10 nM (highlighted) was determined visually without SIEP amplification, while with SIEP, the sensitivity is 100 fold higher at 10 nM (highlighted).

DETAILED DESCRIPTION

Figure 1:
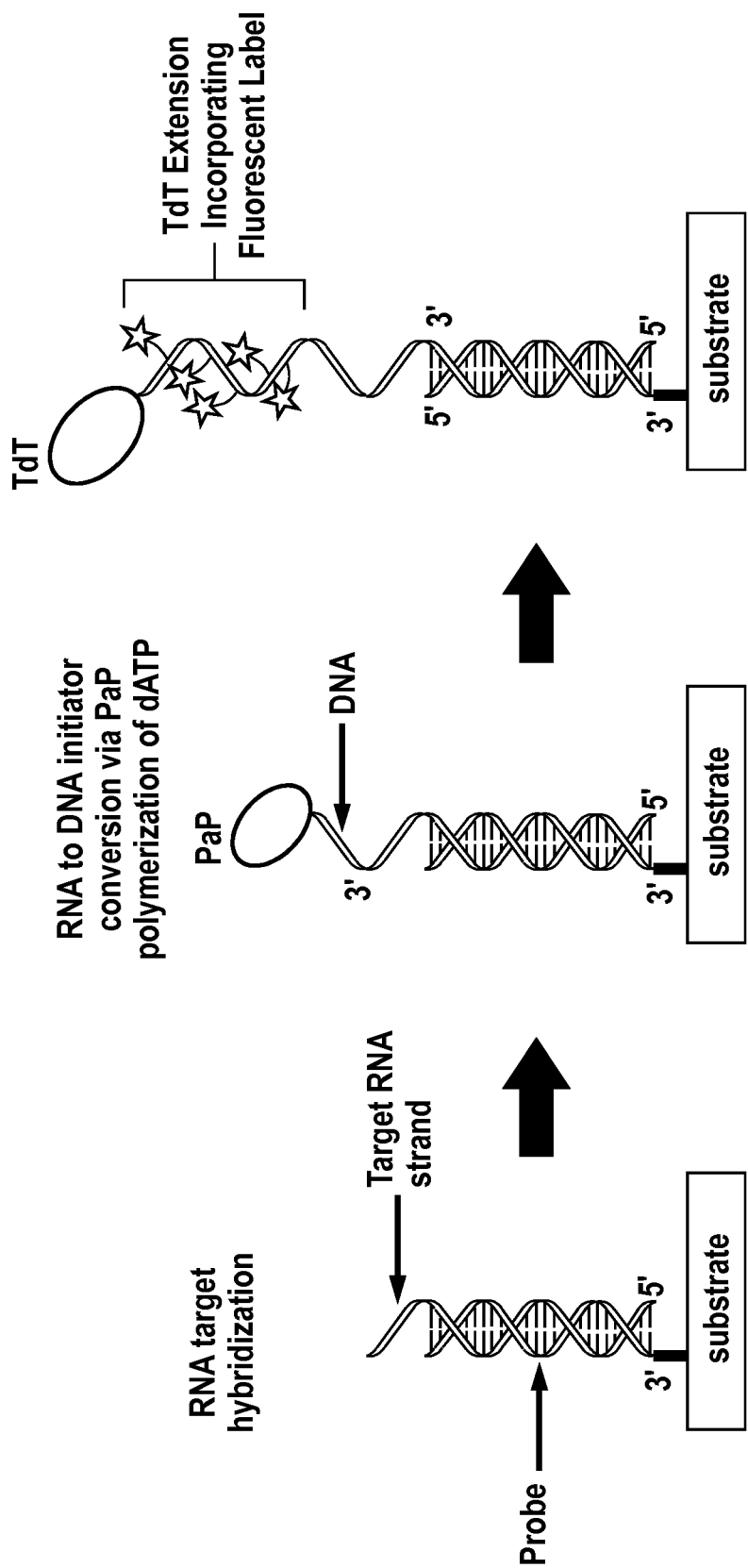
FIG. 1 shows a method of making a fluorescently labeled RNA-DNA extended hybrid that is attached to a support by annealing to a polynucleotide probe.

The details of one or more inventive embodiments are set forth in the accompanying drawings, the claims, and in the description herein. Other features, objects, and advantages of inventive embodiments disclosed and contemplated herein will be apparent from the description and drawings, and from the claims.

As used herein, unless otherwise indicated, the article "a" means one or more unless explicitly otherwise provided for.

As used herein, unless otherwise indicated, terms such as "contain," "containing," "include," "including," and the like mean "comprising."

As used herein, unless otherwise indicated, any embodiment can be combined with any other embodiment.

As used herein, unless otherwise indicated, some inventive embodiments herein contemplate numerical ranges. When ranges are present, the ranges include the range endpoints. Additionally, every subrange and value within the range is present as if explicitly written out.

As used herein, tRNA means transfer RNA.
As used herein, rRNA means ribosomal RNA.
As used herein mRNA means messenger RNA.
As used herein siRNA means small interfering RNA.
As used herein miRNA means micro RNA.
As used herein PNA means peptide nucleic acid.
As used herein, a DNA-RNA hybrid is a single stranded polynucleotide that contains both DNA and RNA. The DNA-RNA hybrid can be annealed e.g., to a polynucleotide probe.

As used herein, a selective probe may bind to more than one target RNA, but does not bind the target RNAs equally.

As used herein, a specific polynucleotide probe binds to only one target RNA.

As used herein, the term "SIEP" or "surface initiated enzymatic polymerization" refers to any of the exemplary or embodied methods described herein.

The methods described herein provide for the development of, in some embodiments, a microarray-based RNA assay that allows direct interrogation of RNA with the following attributes: (1) it can be carried out in situ, i.e., is on-chip; (2) it can ensure that only the analytes of interest (targets) are labeled by introducing a detection label on the target after hybridization, so as to minimize false positive signals and background signal due to non-specific adsorption; (3) it can provide signal amplification by incorporating multiple chromophores, or other labels per binding event, so that the output can be read by low-cost optical scanners or cell phone cameras; and (4) it can be carried out under isothermal conditions to minimize its technological complexity and make it field portable for point-of-care analysis.

Thus, to devise an RNA microarray assay with these attributes, herein we introduce, as one embodiment, a direct RNA detection scheme that involves the direct hybridization of unlabeled RNA molecules with a e.g., printed complementary probe on a non-fouling surface followed by in situ—on-chip—RNA target labeling and signal amplification using surface initiated enzymatic polymerization (SIEP). This assay builds on our previous demonstration that the introduction of a unique 3'-OH moiety due to hybridization of a target DNA to an immobilized probe DNA provides an "initiation" site for the in situ enzyme-catalyzed polymerization of long single stranded DNA (ssDNA) chains that incorporate fluorescently labeled nucleotides. In our original implementation of SIEP, we used terminal deoxynucleotidyl transferase (TdT), a template independent DNA polymerase that catalyzes the sequential addition of deoxynucleotides (dNTPs) at the 3'-OH group of DNA strands and in this process also incorporates multiple fluorescent dNTPs into the polymerized ssDNA. See, Tjong et al. Anal Chem. 83 (13) 2011. and Chow et al. Langmuir 6; 23(23) 2007.

Although TdT is very efficient at catalyzing the growth of DNA from a DNA initiator—the bound target in a target-probe duplex on the surface—and can incorporate multiple unnatural fluorescent nucleotides during SEIP into the growing DNA chain, it does not recognize a RNA initiator efficiently, as would be the case on hybridization of an RNA molecule to a probe on the surface. To solve this problem, herein we show that, surprisingly, the combination of two enzymes: yeast poly(A) polymerase (PaP) and TdT enable the in situ fluorescence detection of RNA molecules using SIEP. PaP is a template independent RNA polymerase that catalyzes polyadenylation at the 3'-OH group of RNA molecules, and has been used for SPR imaging based detection of RNA hybridization to a surface bound probe. PaP however, does not accept fluorescently labeled ribonucleotides, so that in situ SIEP with PaP from an RNA initiator cannot be used for in situ post-hybridization fluorescence labeling and signal amplification of RNA. We have found, however, that PaP has the unusual attribute that it catalyzes the attachment of a few deoxyadenosine triphosphate (dATP) to the 3'-OH of an RNA initiator, creating a RNA-DNA hybrid. The 3'-end of this short DNA sequence can be recognized by TdT, and enables subsequent TdT catalyzed polymerization of a long ssDNA strand with e.g. multiple fluorophores, thereby enabling e.g., in situ fluorescence detection of hybridized RNA. We show that on-chip fluorescent amplification by SIEP has a low picomolar (pM) limit of detection (LOD) for short RNA targets (21-mer) such as miRNA and a LOD of tens of pM for fragmented, in vitro transcribed mRNA with a three orders-of-magnitude dynamic range, and that the assay can be multiplexed in a microarray format.

Disclosed herein are methods for detecting an RNA or DNA target nucleic acid, comprising: a) annealing a target RNA or DNA nucleic acid to a polynucleotide probe; b) extending the annealed target RNA with at least one deoxyribonucleotide triphosphate to form an RNA-DNA hybrid; c) extending the target RNA-DNA hybrid or target DNA with at least one deoxyribonucleotide triphosphate to form an extended target RNA-DNA hybrid or extended target DNA; and d) detecting the presence of the target RNA or target DNA by detecting the presence of the extended target RNA-DNA hybrid or extended target DNA.

In some embodiments, the target RNA or DNA can be derived or obtained from a biological sample. In some aspects, the biological sample can be lysed. In some aspects, the target RNA or DNA can be synthetic and can be a sequence that is found in nature or a sequence that is not found in nature, or a natural or non-natural RNA or DNA fragment thereof.

The biological sample, can be, for example, blood, a biopsy, a tissue biopsy, plasma, lymph, viral, bacterial, a human sample, a diseased human sample, an animal sample, a disease animal sample, saliva, mucus, cerebral spinal fluid, synovial fluid, stomach fluid, intestinal fluid, cytoplasmic fluid, or other type of sample.

The amount of target RNA can be quantified.

The results of the detection of the target RNA can be captured as data, for example, an image the RNA-DNA hybrid can be captured, and the data can be transmitted via a communication medium, for example, a telephone line, the internet, an intranet, a fax, a text, an email, or a letter.

The data can be, for example, a digital image that can be captured, for example, with a digital camera that can be, for example, incorporated into a cell phone e.g., a smart phone.

The inventors have surprisingly found that a target RNA, annealed to a polynucleotide probe, can be enzymatically elongated (e.g., can have DNA bases (deoxyribonucleotides) added) and that the resulting DNA-RNA hybrid, can be detected. The detection can occur, for example, without the use of reverse transcription of RNA to DNA, without amplification of DNA, and without sequencing of the DNA or target RNA.

In some embodiments, the deoxyribonucleotides (e.g., dNTPs) can be added, for example, to an overhanging (e.g., non-annealed) 3'end of a target RNA, where a portion of the target RNA can be annealed to a polynucleotide probe. In some aspects, the dNTPs also have a detectable label.

Fluorescently labeled nucleotides (e.g., dNTPs) may be produced by various techniques, such as those described in Kambara et al., Bio/Technol. 1988. 6:816-21; Smith et al., Nucl. Acid Res. 1985. 13:2399-2412; and Smith et al., Nature. 1986. 321: 674-679, the contents of each of which are herein incorporated by reference for their teachings thereof. The fluorescent dye may be linked to the deoxyribose by a linker arm that is easily cleaved by chemical or enzymatic means. There are numerous linkers and methods for attaching labels to nucleotides, as shown in Oligonucleotides and Analogues: A Practical Approach, IRL Press, Oxford, 1991.; Zuckerman et al., Polynucleotides Res. 1987. 15: 5305-5321; Sharma et al., Polynucleotides Res. 1991. 19:3019; Giusti et al., PCR Methods and Applications, 2:223-227, 1993; U.S. Pat. Nos. 4,757,141; 4,739,044; Agrawal et al., Tetrahedron Letters. 1990. 31:1543-1546; Sproat et al., Polynucleotides Res. 1987. 15:4837; and Nelson et al., Polynucleotides Res. 1989. 17:7187-7194, the contents of each of which are herein incorporated by reference for their teachings thereof. Extensive guidance exists in the literature for derivatizing fluorophore and quencher molecules for covalent attachment via common reactive groups that may be added to a nucleotide. Many linking moieties and methods for attaching fluorophore moieties to nucleotides also exist, as described in Oligonucleotides and Analogues, supra; Guisti et al., supra; Agrawal et al., supra; and Sproat et al., supra.

In one embodiment, the dNTPs are labeled such that the extended DNA, RNA, or DNA/RNA hybrid is labeled. According to the methods described herein, nucleotides may include a detectable label that is either directly or indirectly detectable. A label can be a fluorescent dye. Fluorescent dyes can be detected in droplets in real time with high resolution, and the availability of many fluorescent dyes with distinct excitation and emission wavelengths allow monitoring many labels in one experiment. Sets of fluorescent dyes can be selected so as to allow for a simultaneous detection of more than one dye in the same reaction. An exemplary set of dyes that can be detected at the same time include, but are not limited to, Cy3, Cy5, FAM, JOE, TAMRA, ROX, dR110, dR6G, dTAMRA, dROX, or any mixture thereof. Any of those dyes may be used individually or in any combination in the methods described herein. A dye can allow for single molecule detection. Examples for the use of fluorescence methods in single molecule detection have been described by Joo C et al., Annu Rev. Biochem. 2008. 77, 51-76. A large number of fluorescent dyes have been synthesized, and are commercially available in different formats. This includes fluorescent dyes having a linker region and a hydrazine group that allows for coupling to RNA in a reaction with dialdehyde groups. For examples on such compounds refer to the catalog of Invitrogen. The present methods described herein are not limited to the use of a specific fluorescent dye, but different dyes can be applied to the same effect. The linker region may consist of a carbon backbone, may contain sulfur atoms, ketone groups, or diethylene glycol groups, or dodecaethylene glycol groups. The length of the linker can vary where the backbone is a linear molecule of 1 to 20 atoms. A linker may contain groups of atoms that allow for selective removal of the label in a chemical reaction as, for example, disclosed in PCT Patent Publication No. WO2003/048387.

Additional non-limiting examples as used herein of directly detectable labels for nucleotides (e.g., dNTPs or probes) include isotopic and fluorescent moieties incorporated into, usually covalently bonded to, a nucleotide monomeric unit, e.g. dNTP or monomeric unit of a primer or probe. Isotopic moieties or labels (e.g., radiolabels) of interest include $^{32}$P, $^{33}$P, $^{35}$S, $^{125}$I, and the like. Fluorescent moieties or labels of interest include coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. Quantum Dye.™, fluorescent energy transfer dyes, such as thiazole orange-ethidium heterodimer, TOTAB, etc. Labels may also be members of a signal producing system that act in concert with one or more additional members of the same system to provide a detectable signal. Illustrative examples of such labels are members of a specific binding pair, such as ligands, e.g. biotin, fluorescein, digoxigenin, antigen, polyvalent cations, chelator groups and the like, where the members specifically bind to additional members of the signal producing system, where the additional members provide a detectable signal either directly or indirectly, e.g. antibody conjugated to a fluorescent moiety or an enzymatic moiety capable of converting a substrate to a chromogenic product, e.g. alkaline phosphatase conjugate antibody; and the like. U.S. Pat. No. 5,994,076 is incorporated by reference herein for its specific teachings thereof.

Further, non-limiting examples of labels that can be used include, but are not limited to, 5-FAM (also called 5-carboxyfluorescein; also called Spiro(isobenzofuran-1(3H), 9'-(9H)xanthene)-5-carboxylic acid, 3',6'-dihydroxy-3-oxo-6-carboxyfluorescein); 5-Hexachloro-Fluorescein; ([4,7,2',4',5',7'-hexachloro-(3',6'-dipivaloyl-fluorsceinyl)-6-carboxylic acid]); 6-Hexachloro-Fluorescein; ([4,7,2',4',5',7'-hexachloro-(3',6'-dipivaloylfluorsceinyl)-5-carboxylic acid]); 5-Tetrachloro-Fluorescein; ([4,7,2',7'-tetra-chloro-(3',6'-dipivaloylfluorsceinyl)-5-carboxylic acid]); 6-Tetrachloro-Fluorescein; ([4,7,2',7'-tetrachloro-(3',6'-dipivaloylfluorsceinyl)-6-carboxylic acid]); 5-TAMRA (5-carboxytetramethylrhodamine); Xanthylium, 9-(2,4-dicarboxyphenyl)-3,6-bis(dimethyl-amino); 6-TAMRA (6-carboxytetramethylrhodamine); 9-(2,5-dicarboxyphenyl)-3,6-bis(dimethylamino); EDANS (5-((2-aminoethyl)amino)naphthalene-1-sulfonic acid); 1,5-IAEDANS (5-((((2-iodoacetyl)amino)ethyl)amino)naphthalene-1-sulfonic acid); Cy5 (Indodicarbocyanine-5); Cy3 (Indo-dicarbocyanine-3); and BODIPY FL (2,6-dibromo-4,4-difluoro-5,7-dimethyl-4-bora-3a,4a-diaza-s-indacene-3-pr-oprionic acid); Quasar®-670 dye (Biosearch Technologies); Cal Fluor® Orange dye (Biosearch Technologies); Rox dyes; Max dyes (Integrated DNA Technologies), tetrachlorofluorescin (TET), 4,7,2'-trichloro-7'-phenyl-6-carboxyfluorescein (VIC), HEX, Cy3, Cy 3.5, Cy 5, Cy 5.5, Cy 7, tetramethylrhodamine, ROX, and JOE as well as suitable derivatives thereof. The label can be an Alexa Fluor dye, such as Alexa Fluor 350, 405, 430, 488, 532, 546, 555, 568, 594, 633, 647, 660, 680, 700, and 750. The label can be Cascade Blue, Marina Blue, Oregon Green 500, Oregon Green 514, Oregon Green 488, Oregon Green 488-X, Pacific Blue, Rhodamine Green, Rhodol Green, Rhodamine Green-X, Rhodamine Red-X, and Texas Red-X. The label can be at the 5' end of a probe, 3' end of the probe, at both the 5' and 3' end of a probe, or internal to the probe. A unique label can be used to detect each different locus in an experiment, for example two termini of a target polynucleotide, such as mRNA.

Non-limiting examples of dye-hydrazides that can be used for labeling include Alexa Fluor®-hydrazides and salts thereof, 1-pyrenebutanoic acid-hydrazide, 7-diethylamino-coumarin-3-carboxylic acid-hydrazide (DCCH) Cascade Blue® hydrazides and salts thereof, biocytin-hydrazide, 2-acetamido-4-mercaptobutanoic acid-hydrazide (AMBH), BODIPY® FL-hydrazide, biotin-hydrazide, Texas Red®-hydrazide, biocytin-hydrazide, luminol (3-aminophthalhydrazide), and Marina Blue® hydrazide. Non-limiting examples of dye-ethylenediamines that can be used for labeling include 5-dimethylaminonaphthalene-1-(N-(2-aminoethyl))sulfonamide (dansyl ethylenediamine), Cascade Blue® ethylenediamine and salts thereof, N-(2-aminoethyl)-4-amino-3,6-disulfo-1,8-naphthalimide (lucifer yellow ethylenediamine) and salts thereof, N-(biotinoyl)-N'-(iodoacetyl) ethylenediamine, N-(2-aminoethyl)biotinamide, hydrobromide (biotin ethylenediamine), 4,4-difluoro-5,7-dimethyl-4-bora-3a,4a-diaza-s-indacene-3-propionyl ethylenediamine and salts thereof (BODIPY® FL EDA), Lissamine™ rhodamine B ethylenediamine, and DSB-X™ biotin ethylenediamine (desthiobiotin-X ethylenediamine, hydrochloride).

Non-limiting examples of dye-cadaverines that can be used for labeling include 5-dimethylaminonaphthalene-1-(N-(5-aminopentyl))sulfonamide (dansyl cadaverine), 5-(and -6)-((N-(5 aminopentyl) amino) carbonyl) tetramethylrhodamine (tetramethylrhodamine cadaverine), N-(5-aminopentyl)-4-amino-3,6-disulfo-1,8-naphthalimide and salts thereof (lucifer yellow cadaverine), N-(5-aminopentyl)biotinamide and salts thereof (biotin cadaverine), biotin-X cadaverine (5-(((N-(biotinoyl) amino) hexanoyl) amino) pentylamine and salts thereof, Texas Red® cadaverine (Texas Red® C5), 5-(((4-(4,4-difluoro-5-(2-thienyl)-4-bora-3a, 4a-diaza-s-indacene-3-yl) phenoxy) acetyl) amino) pentylamine and salts thereof (BODIPY® TR cadaverine), Oregon Green® cadaverine, Alexa Fluor® cadaverine, and 5-((5-aminopentyl) thioureidyl) fluorescein and salts thereof (fluorescein cadaverine).

Deoxyribonucleotide triphosphates (dNTPs) contain nitrogenous bases which can be, for example, adenine, thymine, guanine, uridine, or cytosine (e.g., dATP, dTTP, dGTP, dUTP, or dCTP).

In some embodiments, the methods described herein can be conducted on a support, which can be a solid support. In some aspects, the methods described herein can be conducted on a layer or portion of the solid support that is associated with a polynucleotide probe. In some aspects, the methods described herein can be conducted on an array or a microarray. In some aspects, the methods described herein can be conducted on a medical device, which can comprise an array or a microarray.

In some embodiments, multiple target RNAs can be detected simultaneously. Controls can be included in the array or microarray. Two or more of the polynucleotide probes can be different when detecting multiple target RNAs. The solid support or medical device or array or microarray can contain, for example, about 5, about 10, about 50, about 100, about 500, about 1000, about 5000, about 10,000, about 20,000, about 50,000, or from about 1 to about 100,000, including all iterations of integers within the specified range, or at least 10, at least 100, at least 1000, at least 10,000, at least 100,000 polynucleotide probes. The polynucleotide probes can be, for example, printed on to the microarray so that the polynucleotide probes occupy defined positions on the array or microarray.

In some embodiments, the solid support or substrate may comprise an assay plate, slide, glass slide, or solid material. The solid support may be organic or inorganic; may be metal (e.g., copper or silver) or non-metal; may be a polymer or nonpolymer; may be conducting, semiconducting or nonconducting (insulating); may be reflecting or nonreflecting; may be porous or nonporous; etc. For example, the solid support may be comprised of polyethylene, polytetrafluoroethylene, gold, silicon, silicon oxide, silicate dioxide, silicon oxynitride, indium, platinum, iridium, indium tin oxide, diamond or diamond-like film, etc.

In some embodiments, the support, solid support, and medical devices can comprise a substrate layer and a non-fouling layer (e.g., comprising bottle brush polymer(s)), wherein the polynucleotide probe is associated with the non-fouling layer. In some aspects, the non-fouling layer comprises a poly(oligo(ethylene glycol) methacrylate) (pOEGMA) brush substrate. See, U.S. Patent Application Publication U.S. 2006/0057180; Hucknell et al., Advanced Materials. 2009. 21(19), 1968-1971 and Hucknell et al., Advanced Materials. 2009. 21(23), 2441-2446, each of which is incorporated by reference herein for the teachings thereof. In some aspects, the non-fouling layer is applied to a substrate or solid support comprising a glass slide. The polynucleotide probe may be covalently or non-covalently associated. In some embodiments, the non-fouling layer is non-covalently or covalently associated with an anchor which is covalently or non-covalently associated with a tether which is covalently bonded to the polynucleotide probe. A spacer may be inserted between the tether and the polynucleotide probe. The spacer may be, for example, an amino acid. The amino acid may be, for example, covalently bound to both the tether and the polynucleotide probe. In this way, the polynucleotide probe, with and without the presence of a spacer, can be anchored to the non-fouling polymer layer but not covalently associated with the non-fouling layer and not directly-non-covalently associated with it as well. Such an association can be, for example, an indirect, non-covalent association.

In some of the embodiments described herein are methods for detecting a target nucleic acid from a sample that contains at least one nucleic acid. In some aspects, the nucleic acid comprises DNA or RNA. In some aspects, the nucleic acid is annealed to a probe. In some aspects, the hybridized nucleic acid is extended using a nucleic acid polymerase. In some aspects, the extended nucleic acid comprises DNA, RNA, or a DNA/RNA hybrid molecule. In some further aspects, the presence or level of the extended target nucleic acid is detected by fluorescence or colorimetric detection methods.

In one embodiment described herein, an isolated nucleic acid is annealed to a probe. In one aspect, the probe comprises a DNA molecule. In another aspect, the probe comprises an RNA molecule. In another aspect, the probe comprises a PNA molecule. In another aspect, the probe comprising a DNA molecule, RNA molecule or a PNA molecule may be labeled with one or more detectable labels as described herein. In another aspect, the probe comprising a DNA molecule, RNA molecule or a PNA molecule may comprise from at least about 1 nitrogenous base to about 100 nitrogenous bases in length, including all iterations of integers within the specified range. In another aspect, the probe comprising a DNA molecule, RNA molecule or a PNA molecule may comprise from at least about 5 nitrogenous bases to about 35 nitrogenous bases in length, including all iterations of integers within the specified range. In another aspect, the probe comprising a DNA molecule, RNA molecule or a PNA molecule may comprise from at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50 nitrogenous bases.

In some of the embodiments described herein, the probe comprises a nitrogenous base comprising a purine or pyrimidine base comprising adenine, guanine, cytosine, thymine, or uracil, and any artificially modified or synthetic derivative thereof. In some other aspects, the nitrogenous base may be a part of a ribonucleoside. In some other aspects, the nitrogenous base may be a part of a deoxyribonucleoside. In some other aspects, the nitrogenous base may be part of a dideoxyribonucleoside. In some other aspects, the nitrogenous base may be a part of a ribonucleotide. In some other aspects, the nitrogenous base may be a part of a deoxyribonucleotide. In some other aspects, the nitrogenous base may be part of a dideoxyribonucleotide. In some other aspects, the nitrogenous base may be part of a larger DNA molecule. In some other aspects, the nitrogenous base may be part of a larger RNA molecule. In some other aspects, the nitrogenous base may be part of a larger PNA molecule.

In some of the embodiments described herein, the probe may comprise a peptide nucleic acid (PNA). A PNA molecule is a synthetic nucleic acid analogue with a pseudo-peptide backbone in which the phosphodiester backbone present in e.g. DNA or RNA is replaced by repetitive units of short aliphatic moieties with an amino end and a carboxylic end, forming an amide bond in the oligomer or polymer. To the short aliphatic moieties of the backbone, nucleobases, usually purine and pyrimidine bases, are attached via a side chain, generally a methyl carbonyl linker. In some aspects a PNA molecule may comprise any desired nucleobase, including purine and pyrimidine bases, may be used. Examples of suitable purine and pyrimidine bases include, but are not limited to, cytosine, 5-methylcytosine, guanine, adenine, thymine, uracil, 5,6-dihydrouracil, hypoxanthine, xanthine, ribothymine, 7-methylguanine or 7-isobutylguanine. A number of further suitable illustrative nucleobases that may also be termed "modified" nucleobases have recently been reviewed by Wojciechowski & Hudson (Current Topics in Medicinal Chemistry (2007) 7, 667-679). These include inter alia 4-(1,2,4-triazolyl)thymine, 5-alkynyluracil, 5-iodouracil, thiouracil, 5-(propargyl alcohol)uracil, isocytosine, pseudoisocytosine, 5-(ferrocenylpropargyl-carboxamide)uracil, N6-alkyladenine, N7-xanthine, 3-nitropyrrole, 6-thioguanine, phenoxazine, 2-aminopurine or 2,6-diaminopurine.

In some embodiments, the PNA molecule may be further modified with an acetyl group and one or more spacer amino acids. In some aspects, the acetyl group may be positioned on the 5' end of the PNA molecule. In some other aspects, the one or more spacer amino acids may be positioned on the 3' end of the PNA molecule. In one aspect, the one or more spacer amino acids comprise a lysine residue. In another aspect, the one or more spacer amino acids are covalently bound to a linking agent comprising biotin.

In some aspects, the PNA molecule may comprise about 1 to about 35 nucleobases (e.g., any of the nucleobases or nitrogenous bases described herein), including all iterations of integers within the specified range. In some other aspects, the PNA molecule may comprise about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50 nucleobases (e.g., any of the nucleobases or nitrogenous bases described herein). See, U.S. Patent Application Publication 2011/0245458, which is incorporated by reference herein for its specific teachings of PNA molecules.

In some embodiments, the probe is immobilized on a solid support. In some aspects, the probe may be modified with biotin and immobilized on a substrate coated with streptavidin. Other probe or nucleic acid immobilization techniques known in the art are contemplated by the methods described herein.

In some of the embodiments described herein, the target nucleic acid is annealed to a probe described herein in a suitable buffer. In one aspect, the target nucleic acid is annealed to a probe for at least about 10 minutes to about 24 hours, including all iterations of integers within the specified range. In another aspect, the target nucleic acid is annealed to a probe at a temperature of about 22° C. to about 90° C. including all iterations of integers within the specified range. In one aspect, the target nucleic acid is annealed to a probe at a temperature of about 42° C. for at least about 15 hours.

In some of the embodiments described herein, the target nucleic acid is dephosphorylated. In one aspect, the target nucleic acid is dephosphorylated before being hybridized to a probe as described herein. In another aspect, the target nucleic acid is dephosphorylated after being hybridized to a probe as described herein.

In some of the embodiments described herein, a target nucleic acid is extended by a polymerase. The polymerase may be any polymerase available that is able to extend a nucleic acid. Exemplary non-limiting polymerases include DNA polymerase I (klenow fragment), II, III, or IV; RNA polymerase I, II, or III; T7 RNA polymerase, reverse transcriptase, terminal deoxynucleotidyl transferase (TdT) or poly(A) polymerase (PaP). In some aspects, the target nucleic acid is extended with a polymerase comprising TdT. In some other aspects, the target nucleic acid is extended with a polymerase comprising PaP. In some other aspects, the target nucleic acid is extended with a polymerase comprising PaP followed by TdT.

Additional non-limiting examples of nucleic acid polymerases generally useful in the methods described herein include DNA polymerases, RNA polymerases, reverse transcriptases, and mutant or altered forms of any of the foregoing. DNA polymerases and their properties are described in detail in, among other places, DNA Replication 2nd edition, Kornberg and Baker, W. H. Freeman, New York, N.Y. 1991. Known conventional DNA polymerases include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent™ DNA polymerase, Cariello et al., 1991, Polynucleotides Res, 19: 4193, New England Biolabs), 9°Nm™ DNA polymerase (New England Biolabs), Stoffel fragment, ThermoSequenase® (Amersham Pharmacia Biotech UK), Therminator™ (New England Biolabs), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol., 127: 1550), DNA polymerase, *Pyrococcus kodakaraensis* KOD DNA polymerase (Takagi et al., 1997, Appl. Environ. Microbiol. 63:4504), JDF-3 DNA polymerase (from *Thermococcus* sp. JDF-3, Patent application WO 0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *Thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al., 1981, J. Biol. Chem. 256:3112), and archaeal DP1I/DP2 DNA polymerase II (Cann et al, 1998, Proc. Natl. Acad. Sci. USA 95:14250).

Both mesophilic polymerases and thermophilic polymerases are contemplated. Thermophilic DNA polymerases include, but are not limited to, ThermoSequenase®, 9°Nm™, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof.

Reverse transcriptases include, but are not limited to, reverse transcriptases from HIV, HTLV-1, HTLV-II, FeLV, FIV, SIV, AMV, MMTV, MoMuLV and other retroviruses (see Levin, Cell 88:5-8 (1997); Verma, Biochim Biophys Acta. 473:1-38 (1977); Wu et al., CRC Crit. Rev Biochem. 3:289-347 (1975)).

In some embodiments described herein, a target nucleic acid is extended with a polymerase comprising TdT and/or PaP. In some aspects, the extension reaction occurs after the target nucleic acid is hybridized to a probe described herein. In some aspects, the probe may be bound to a solid support or unbound in an appropriate reaction solution. In some aspects, a DNA target nucleic acid is extended with a polymerase comprising TdT. In some aspects, an RNA target nucleic acid is extended with a polymerase comprising PaP. In some aspects, an RNA target nucleic acid is extended first with PaP followed by a separate extension reaction with TdT. In some other aspects, an RNA target nucleic acid is extended with PaP and TdT in the same reaction.

In some embodiments described herein, a target DNA nucleic acid is extended by an extension reaction with a polymerase comprising TdT. In some aspects the extension reaction is performed following hybridization of the target DNA nucleic acid to a probe described herein. In some aspects, the number of nucleic acids incorporated in the target DNA nucleic acid is from 1 to about 1,000, about 1 to 500, about 1 to 150, about 1 to 100, about 1 to 90, about 1 to 70, about 1 to 50, about 1 to 40, about 1 to 30, about 1 to 20, about 1 to 10, about 1 to 5, including all iterations of integers within the specified ranges, or about 5, about 10, about 15, about 20, about 25, about 30, about 35, about 40, about 45, about 50, about 60, about 70, about 80, about 90, about 100, about 200, about 300, about 400, about 500, or about 1000 nucleic acids. In some aspects, the incorporated nucleic acid comprises dATP, dCTP, dGTP, or dTTP.

In some embodiments described herein, a target RNA nucleic acid is extended by an extension reaction with a polymerase comprising PaP. In some aspects the extension reaction is performed following hybridization of the target RNA nucleic acid to a probe described herein. In some aspects, the number of nucleic acids incorporated in the target RNA nucleic acid is from 1 to about 1,000, about 1 to 500, about 1 to 150, about 1 to 100, about 1 to 90, about 1 to 70, about 1 to 50, about 1 to 40, about 1 to 30, about 1 to 20, about 1 to 10, about 1 to 5, including all iterations of integers within the specified range, or about 5, about 10, about 15, about 20, about 25, about 30, about 35, about 40, about 45, about 50, about 60, about 70, about 80, about 90, about 100, about 200, about 300, about 400, about 500, or about 1000 nucleic acids. In some aspects, the incorporated nucleic acid comprises ATP or dATP.

In some embodiments, an extension reaction is performed to generate an RNA/DNA hybrid molecule. In some aspects the extension reaction leading to the generation of an RNA/DNA hybrid molecule is performed following hybridization to a probe described herein. In some aspects, a target RNA molecule is treated with PaP in the presence of a deoxyribonucleotide (e.g., dATP) to form a RNA/DNA hybrid. Surprisingly, it was found that PaP, which normally catalyzes the incorporation of multiple ATP to the 3' position of an RNA molecule, was able to incorporate at least one dATP molecule to the 3' position of an RNA molecule. Thus, using this previously unknown attribute of PaP, it is possible to generate an RNA/DNA hybrid molecule.

In some other aspects, the number of incorporated nucleic acids to generate the RNA/DNA hybrid target nucleic acid molecule may comprise from at least about 1 to about 250 nucleic acids, including all iterations of integers within the specified range. In some other aspects, the number of incorporated nucleic acids to generate the RNA/DNA hybrid target nucleic acid molecule may comprise from at least about 10 to about 100 nucleic acids, including all iterations of integers within the specified range. In some other aspects, the number of incorporated nucleic acids to generate the RNA/DNA hybrid target nucleic acid molecule may comprise from 1 to about 20, from 1 to about 15, from 1 to about 10, from 1 to about 5, from 1 to about 3, or from 1 to about 2 nucleic acids, including all iterations of integers within the specified ranges. In some aspects, the incorporated nucleic acid comprises dATP.

In some embodiments described herein, a target RNA/DNA hybrid nucleic acid is extended by an extension reaction with a polymerase comprising TdT. In some aspects, the number of nucleic acids incorporated in the target DNA nucleic acid is from 1 to about 1,000, about 1 to 500, about 1 to 150, about 1 to 100, about 1 to 90, about 1 to 70, about 1 to 50, about 1 to 40, about 1 to 30, about 1 to 20, about 1 to 10, about 1 to 5, including all iterations of integers within the specified range, or about 5, about 10, about 15, about 20, about 25, about 30, about 35, about 40, about 45, about 50, about 60, about 70, about 80, about 90, about 100, about 200, about 300, about 400, about 500, or about 1000 nucleic acids. In some aspects, the incorporated nucleic acid comprises a nucleotide comprising dATP, dCTP, dGTP, dTTP or dUTP.

In some embodiments, the nucleic acids incorporated into the extended target RNA, DNA, or RNA/DNA hybrid as described herein comprise at least one or more labeled nucleotides. In some aspects, the nucleotide comprises a labeled dNTP (e.g., dATP, dCTP, dUTP, dTTP, or dGTP). In one aspect, the incorporated labeled nucleotide comprises Cy3-dATP. In some aspects, the molar ratio of labeled dNTPs to unlabeled dNTPs may be from about 5:1 to about 1:500, including all iterations of ratios within the specified range. In some other aspects, the molar ratio of labeled dNTPs to unlabeled dNTPs was from about 1:1 to about 1:100, including all iterations of ratios within the specified range. In some other aspects, the molar ratio of labeled dNTPs to unlabeled dNTPs may be from about 1:5, about 1:10, about 1:20, about 1:50, and about 1:100. In some aspects, the total concentration of dNTPs (e.g., labeled dNTPs and unlabeled dNTPs at the specified ratios) in an extension reaction was from about 0.01 mM to about 1 mM, including all iterations of integers within the specified range. In one aspect, the total concentration of dNTPs (e.g., labeled dNTPs and unlabeled dNTPs at the specified ratios) may be about 0.1 mM, about 0.2 mM, about 0.3 mM, about 0.4 mM, about 0.5 mM, about 0.6 mM, about 0.7 mM, about 0.8 mM, about 0.9 mM, or about 1 mM.

In some embodiments, the target RNA, DNA, or RNA/DNA hybrid nucleic acid may be extended with an unlabeled dNTP and without any labeled dNTPs. In some aspects, the extended target nucleic acid may be detected with a secondary detection reagent. In some aspects, the secondary detection reagent comprises detectable metallic nanoparticles, which are able to bind to nucleic acids and are directly detectable or indirectly detectable depending on the chosen nano-particle as is known in the art. In some aspects, these metallic nanoparticles may be positively charged. In some aspects, these metallic nanoparticles may be spherical or rod shaped. These alternative embodiments simplify the detection methods by eliminating the need for specialized fluorescent microscopes or fluorescent scanning equipment, while maintaining a high level of sensitivity and a low limit of detection (LOD).

Metallic nanoparticles useful for the methods described herein include metal (e. g., gold, silver, copper and platinum), semiconductor (e.g., CdSe, CdS, and CdS or CdSe coated with ZnS) and magnetic (e.g., ferromagnetite) colloidal materials. Other nanoparticles contemplated by the methods described herein include ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs. The size of the metallic nanoparticles can be from about 5 nm to about 150 nm (mean diameter), from about 5 to about 50 nm, or from about 10 to about 30 nm, including all iterations of integers within the specified ranges.

Methods of making metal, semiconductor and magnetic nanoparticles are well-known in the art. See, e.g., Schmid, G. (ed.) Clusters and Colloids (V C H, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988).

Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs nanoparticles are also known in the art. See, e.g., Weller, Angew. Chem. Int. Ed. Engl., 32, 41(1993); Henglein, Top. Curr. Chem., 143, 113 (1988); Henglein, Chem. Rev., 89, 1861 (1989); Brus, Appl. Phys. A., 53, 465 (1991); Bahncmann, in Photochemical Conversion and Storage of Solar Energy (eds. Pelizetti and Schiavello 1991), page 251; Wang and Herron, J. Phys. Chem., 95, 525 (1991); Olshaysky et al., J. Am. Chem. Soc., 112, 9438 (1990); Ushida et al., J. Phys. Chem., 95, 5382 (1992).

Methods of making gold nanoparticles (AuNPs) are well known in the art; the reduction of aqueous gold salts is the most widely used method of preparing AuNPs in solution. Introducing agents (such as thiols, amines, phosphines, polymers and surfactants) during synthesis provides an exceptional degree of morphological and size control in the preparation of AuNPs. For example, see Brust. M, et al. J. Chem. Soc., Chem. Commun. 1994. 801. In some embodiments, the AuNPs described herein are stabilized with cetyltrimethylammonium bromide (CTAB). In some embodiments, the AuNPs described herein are stabilized with citrate. In some aspects, citrate stabilized AuNPs are further modified with thiol-polyethylene glycol-amine. See, DeLong et al., Annu Rev. Biochem. 2010. Nanotechnol Sci Appl. 3, 53-63, which is incorporated herein by reference for its teachings thereof.

In some embodiments, the extended target nucleic acids may be detected with a secondary detection reagent comprising gold nanoparticles (AuNPs), which bind to nucleic acids. Without being bound by any theory, nucleic acids interact with AuNPs due to the interaction of the positively charged Au and negatively charged nucleic acid phosphate backbone structure. See, Li and Rothberg., PNAS. 2004. 39(101), 14036-14039 and Kanjanawarut and Su., Anal. Chem. 2009. 81, 6122-6129 and U.S. Pat. No. 6,361,944, each of which are incorporated herein by reference for their specific teachings of AuNPs. Furthermore, the principle of AuNPs as detection reagents relies on the unique surface plasmon resonance properties of AuNPs; that is, the well-dispersed AuNP appears red in color, whereas the aggregated AuNPs have a blue (or purple) color. A target analyte or a biological process that triggers (directly or indirectly) AuNP aggregation (or redispersion of aggregates) can in principle be detected by color changes. As the interparticle plasmon coupling yields a huge absorption band shift (up to 300 nm), the color change can be observed by the naked eye, and therefore, no sophisticated instruments are necessarily required. Quantitative analysis can be realized by recording the absorption spectra (normally at an arbitrarily chosen assay time given the fact that AuNP aggregation is a dynamic and continuous process) using a standard spectrophotometer or a flatbed scanner coupled with a computer or software capable of calculating pixel densities.

In some aspects, the number of incorporated unlabeled dNTPs in the extended target nucleic acid increases the number AuNPs that may associate with the target nucleic acid, thereby increasing the density of aggregation of AuNPs and the detection sensitivity of the assay. In some aspects, the sensitivity of the methods described herein is at least about 10 fold to about 100 fold higher following the extension of the target DNA, RNA, or DNA/RNA hybrid nucleic acid when compared to the non-extended target nucleic acids. In some further aspects, the number of incorporated unlabeled dNTPs in the extended target nucleic acid may be optimized for the detection of low concentration target nucleic acids. Thus, in some aspects, the methods described herein have a LOD of a target nucleic acid (e.g., target DNA, RNA, or DNA/RNA hybrid) of at least about 100 pM.

In some embodiments, the individual sizes of the AuNPs that are useful in the methods described herein are less than about 0.001 nm to less than about 1000 nms. In some other embodiments, the individual sizes of the AuNPs that are useful in the methods described herein are less than about 1 nm to less than about 50 nm. In some aspects, the size of the AuNPs can be less than about 0.001, less than about 0.05 nm, less than about 1 nm, less than about 1.5 nm, less than about 2 nm, less than about 2.5 nm, less than about 3 nm, less than about 3.5 nm, less than about 4 nm, less than about 4.5 nm, less than about 5 nm, less than about 6 nm, less than about 7 nm, less than about 8 nm, less than about 9 nm, less than about 10 nm, less than about 12 nm, less than about 14 nm, less than about 16 nm, less than about 18 nm, less than about 20 nm, less than about 25 nm, less than about 30 nm, less than about 35 nm, less than about 40 nm, less than about 45 nm, less than about 50 nm, less than about 100 nm, less than about 500 nm, or less than about 1000 nm.

In some embodiments, the sensitivity of the methods described herein is higher for the detection of an extended target RNA nucleic acid than an extended target DNA nucleic acid. In some aspects the sensitivity of detecting an extended target RNA nucleic acid is about 5 fold to about 20 fold more sensitive than an extended target DNA nucleic acid by the methods described herein. Without being bound by any theory, it is thought that this increase in sensivity towards an RNA target nucleic acid is because of a higher affinity of PNA probes towards RNA compared to DNA. See, Jenson et al., Biochemistry. 1997. 36(16), 5072-5077.

Some embodiments of the methods described herein further comprise kits.

The kits described herein can comprise supports, solid supports, and medical devices herein. Kits can include instructions, for example written instructions, on how to use the material(s) therein. Material(s) can be, for example, any substance, composition, polynucleotide, solution, etc, herein or in any patent, patent application publication, reference, or article that is incorporated by reference.

In some embodiments, described herein are methods of diagnosing a disease or condition, the method comprising, diagnosing the disease or condition by detecting a target RNA associated with the disease or condition by: a) annealing the target RNA to a polynucleotide probe; b) extending the annealed target RNA with at least one deoxyribonucleotide triphosphate to form an RNA-DNA hybrid; c) extending the RNA-DNA hybrid with at least one deoxyribonucleotide triphosphate to form an extended RNA-DNA hybrid; and d) diagnosing the disease or condition by detecting the presence of the target RNA by detecting the extended RNA-DNA hybrid.

In some embodiments, the methods described herein can be used to diagnose a disease or condition when the presence of a target RNA associated with the disease or condition is detected. Without being limiting, the disease or condition can be, for example, human immunodeficiency virus (HIV), herpes simplex virus (HSV), herpes simplex virus-1 (HSV-1), herpes simplex virus-2 (HSV-2), human papillomavirus (HPV), human papillomavirus-16 (HPV-16), human papillomavirus-18 (HPV-18), hepatitis C virus (HCV), hepatitis B virus (HBV), hepatitis A virus (HVA), cytomegalovirus, tuberculosis, Chlamydia, gonorrhea, syphilis, Methicillin-resistant Staphylococcus aureus (MRSA), mumps, measles, cholera, typhoid fever, rheumatic fever, cancer, stroke, ischemic disease, cardiovascular disease, Lyme disease, rabies, influenza, Ebola, pregnancy, a fungal infection, a bacterial infection, polio, small pox, diabetes, diabetes type I, diabetes type II, a viral infection, an autoimmune disease, a neurodegenerative disease, and any combination thereof.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Fluorescence Detection of RNA Microarrays by Surface Initiated Enzymatic Polymerization Example 1

RNA Extension and Labeling in Solution

In at least some RNA extension reactions, the concentration of RNA primer that acts as the initiator (I) for SIEP was e.g. 1000 fold less than that of the monomer nucleotides (M) to drive the polymerization of an RNA chain. The ratio of fluorescent dNTPs to natural dNTP were e.g. 1:5, 1:10, 1:20, 1:50, and 1:100 at ~1 mM total monomer concentration (M).

(1) Reaction with TdT: a reaction mixture consisting of 1 µM Cy5-labeled RNA primer [5'-Cy5-rA10], 1 mM dATP monomers, various amounts of Cy3-dATP, and 10 U of TdT in 20 µL, of TdT buffer (1×, 100 mM potassium cacodylate, 1 mM CoCl2, and 0.2 mM DTT, pH 7.2) were incubated at 37° C. for 2 h.

(2) "One pot" reaction with PaP and TdT: a reaction mixture consisting of 1 µM RNA primer [5'-Cy5-rA10], 1 mM dATP monomers, various amounts of Cy3-dATP, 600 U of PaP in PaP buffer (1×, 20 mM Tris-HCl, 0.6 mM MnCl2, 20 µM EDTA, 0.2 mM DTT, 100 µg/ml acetylated BSA, 10% glycerol, pH 7.0) and 10 U of TdT in TdT buffer (1×) in 20 µl total reaction volume were incubated at 37° C. for 2 h.

(3) Sequential PaP and TdT reactions were carried out in two steps: in the first step, a mixture of 1 µM RNA primer [5'-Cy5-rA10], 1 mM dATP monomers, and 600 U of PaP in 10 µL, of PaP buffer (1×) was incubated at 37° C. for 1 h. Without an intervening purification step, in the second step, various amounts of Cy3-dATP and 10 U of TdT in TdT buffer (1×) were added to the reaction mixture to make up a total of 20 µL of reaction and further incubated at 37° C. for 2 h.

A control reaction was carried out similarly using Cy5-labeled DNA primer as the initiator [5'-Cy5-dA10] with 1 mM dATP as the monomer to compare the efficiency of RNA and DNA primer extension using TdT.

Example 2

Determination of the Number of Fluorescent Nucleotides Incorporated per RNA Chain For each type of extension reaction, the reaction product was subjected to a purification step to remove the non-extended primer (<20 bases) and unreacted monomers, by adding filtered water to make up a 50 µl mixture and passing it through a Probe Quant™ G50 spin column (GE Healthcare). To determine the mole fraction of initiator that was extended and the number of fluorescent dNTPs that were incorporated into the polymerized DNA, the purified product was then diluted with 100 µL deionized water, and its fluorescence was measured on a Victor3™ microplate reader (Perkin Elmer Life Sciences) using two sets of excitation and emission filters for Cy5 and Cy3 fluorescence measurement. The amount of initiator and fluorescent dNTPs was determined by establishing a linear standard curve. The average number of fluorescent dNTPs per DNA chain was determined by dividing the total amount of fluorophores by the amount of primer. The initiation efficiency of the extended primer (% primer extended) is determined relative to the input primer amount in the reaction.

Example 3

On-Chip Fluorescent Labeling of RNA Hybridization by SIEP

We selected a DNA sequence from the glyceraldehyde 3-phosphate dehydrogenase (GAPDH) gene as a model system to test our assay. The fully complementary 5'-biotinylated 17-mer PNA probe [5'-Ac-GTC CAC CAC CCT GTT GC-lysine-biotin-3', 1 µM] (DNA sequence shown in SEQ ID NO: 1) and non-specific PNA probe derived from the hepatitis B virus (HBV) sequence [5'-Ac-ACC TTG TCA TGT ACC AT-lysine-biotin-3', 1 µM] (DNA sequence shown in SEQ ID NO: 2) were individually mixed with streptavidin (2.5 µM) and then spotted using a non-contact printer (Piezzorray, Perkin Elmer) on a nonfouling poly (oligo(ethylene glycol) methacrylate) (POEGMA) brush grown on a glass substrate. The slides spotted with the probes were then incubated overnight in a vacuum chamber and rinsed with 1×SSC buffer containing 0.1% Tween 20 before use. A dose-response curve of hybridized target was generated by incubating the printed probes with a solution of the target RNA that covered a 1 pM-1 µM concentration range. Each target solution was heated at 95° C. for 10 min prior to hybridization, then quenched in ice and incubated with the printed probe. We carried out the assay using two targets: (1) a 21-mer synthetic RNA target [5'-rGrCrA rArCrA rGrGrGrUrGrG rUrGrG rArCrC rUrCrA-3'] (SEQ ID NO: 3) that is complementary to the probe; and (2) full length in vitro transcribed GAPDH mRNA (~1.4 Kb, details found in SI). Each target was incubated overnight (~16 h) with mild shaking at 42° C. in the hybridization buffer (3×SSC, 0.1% Tween 20, and 4.95 M urea). The synthetic RNA was used as received while the in vitro transcribed GAPDH mRNA was either used as received or fragmented (details in SI) by incubation in the fragmentation reagent at 70° C. for 15 min. For fragmented RNA targets, after rinsing (3×) with wash buffer (1×SCC, 0.1% Tween 20), the bound fragmented RNA target was enzymatically dephosphorylated on-chip (0.0625 U/µ 1 phosphatase in 0.125% BSA and 0.1% Tween 20) at 37° C. for 1 h to ensure the availability of the 3'-OH. The 3'-OH of the bound RNA target was then converted to a DNA-RNA hybrid by SIEP using PaP to incorporate a short oligo-dATP (6 U/µ 1 PaP and 500 µM dATP in 1× PaP buffer) at 37° C. for 2 h, followed by SIEP using TdT to incorporate Cy5-dATP (0.1 U/µ 1 TdT, 100 1AM dATP and 0.5 1AM Cy3-dATP in 1× TdT buffer) at 37° C. for 1 h. The slides were then rinsed in 1×SSC buffer with 0.1% Tween 20 for 30 min and scanned immediately on a GenePix scanner. The average signal intensity of the spot (background subtracted) was then plotted as a function of the target RNA concentration.

Example 4

Multiplexed Detection of mRNA Via SIEP

We printed a PNA probe for GAPDH gene, serine protease 21 (PRSS21) gene [5'-Ac-CTT CGG TGA CTC AGG TG-lysine-biotin-3', 1 µM] (DNA sequence shown in SEQ ID NO: 4), and interferon-induced protein 44 (IF144) gene [5'-Ac-CTG AGA CGA ATG CTA TG-lysine-biotin-3', 1 µM] (DNA sequence shown in SEQ ID NO: 5) as individual spots on a polymer brush substrate. These probes were then exposed to a mixture of fragmented of mRNA targets (corresponding in vitro transcribed GAPDH, PRSS21, and IF144 mRNA targets) spiked into the hybridization buffer. Following overnight hybridization step at 42° C., the targets 20 were treated for the on-chip dephosphorylation step and the on-chip labeling steps as described earlier.

Example 5

Additional Study Materials

Cy5-labeled RNA oligonucleotide primer [5'-Cy5-rA10], synthetic RNA target, and PNA probes were synthesized by Gene Link, Integrated DNA Technologies, Panagene (Daejeon, Korea), respectively. TdT enzyme, TdT buffer, and dATP were purchased from Promega while Cy3-dATP was purchased from Perkin Elmer. Yeast PaP and buffer were supplied by Affymetrix, while antarctic phosphatase was purchased from New England Biolabs. Plasmids containing the genes for GAPDH, PRSS21, and IFI44 were purchased from ATCC. The in vitro transcription kit (Ambion MEGAscript Kits, SP6 promoter) to express the full length mRNA from these plasmids was purchased from Ambion. Top Vision LE GQ agarose was supplied by Fermentas. Phosphate buffer and Tween 20 were purchased from Sigma-Aldrich.

Example 6

Fragmented RNA Extension and Labeling

In vitro transcribed mRNA (~1 µg/ml) was incubated in the RNA fragmentation reagent from Ambion Inc. at 70° C. for 15 min and purified as well as concentrated using Amicon Ultra filter (Millipore) with 3000 molecular weight cut off. A fraction of fragmented RNA was then reacted with phosphatase (0.25 U/µl Antarctic phosphatase and 0.05% BSA in 1× phosphatase buffer) and further purified using Amicon Ultra filter. About 300 ng of fragmented RNA (as initiator) was then reacted following the sequential reaction protocol (3) using PaP and TdT, with dATP and Cy3-dATP as the monomers.

Example 7

LOD Determination and Instrumentation

LOD was determined by determining the concentration that corresponds to the signal at zero concentration plus three times the standard deviation from the sigmoidal curve fit of the target versus concentration ("dose-response") curve.
The incorporation of fluorescent nucleotides in solution was determined by fluorescence measurements on a Victor3™ microplate reader (Perkin Elmer Life Sciences). For Cy5 fluorescence measurement, an excitation band filter of 650±4 nm and an emission band filter of 680±5 nm was used, while for Cy3 fluorescence measurement, a 560±4 nm excitation band filter and a 590±10 nm emission band filter was used. On-chip TdT labeling was determined by scanning the glass slides for the Cy5 (635 nm) and Cy3 (532 nm) fluorescent signal using an Axon GenePix Pro 4200 scanner (Molecular Devices) at 10 µm resolution with optimized PMT and gain settings.

Example 8

RNA Labeling by DNA Polymerization Using TdT

RNA samples isolated from cells or tissues are generally chemically or enzymatically labeled prior to detection. Chemical labeling of RNA samples is accomplished through reactive chemistries such as periodate, activated phosphate or activated succinimide esters, thiol, or "click" chemistry. These labeling strategies chemically attach labels internally or at the end of the RNA chain. Enzymatic labeling of RNA offers another option for site selective attachment of labels. Examples include: T7 RNA polymerase that incorporates various guanosine analogs into RNA transcripts during in vitro transcription; T4 polynucleotide kinase (PNK) that transfers a radioactive phosphate from ATP to the 5'-end of RNA;25 T4 RNA ligase that incorporates radioactive dNTPs, fluorescent dinucleotides, and biotinylated short oligonucleotide at the 3'-end of RNA; Klenow fragment of DNA polymerase I that incorporates biotinylated dNTPs into RNA primer according to the template DNA strand; Yeast Poly(A) polymerase (PaP) that incorporates radioactive cordycepin triphosphate, biotin-ATP, digoxigenin-UTP (DIG-UTP) and a limited number of fluorescein-ATP;29 and terminal deoxynucleotidyl transferase (TdT) that incorporates a limited number of biotin-dUTP or DIG-dUTP at the 3'-end of RNA.
We previously reported the direct incorporation of multiple fluorescent dNTPs into a ssDNA chain from a short oligonucleotide DNA initiator by TdT catalyzed DNA polymerization. We showed that long (>1 Kb) homopolymer ssDNA could be polymerized from short DNA initiators (~10 bases) and that up to ~50 fluorescent Cy-3 labeled dNTPs could be incorporated per kilobase of DNA.17 Although there is a report of RNA labeling by incorporating a few DIG- or biotin-dUTP as at the 3'-end of RNA using TdT, investigation of the direct labeling of RNA with fluorescent dNTPs using TdT has not been previously reported. We hence examined TdT's ability to directly incorporate multiple fluorescent dNTPs (Cy3-dNTPs) for amplified RNA labeling. Throughout the paper, we often refer to the RNA primer as "initiator" and the nucleotides as "monomers" to place the reaction of TdT catalyzed DNA growth in the context of surface initiated chemical polymerization.

Figure 2:
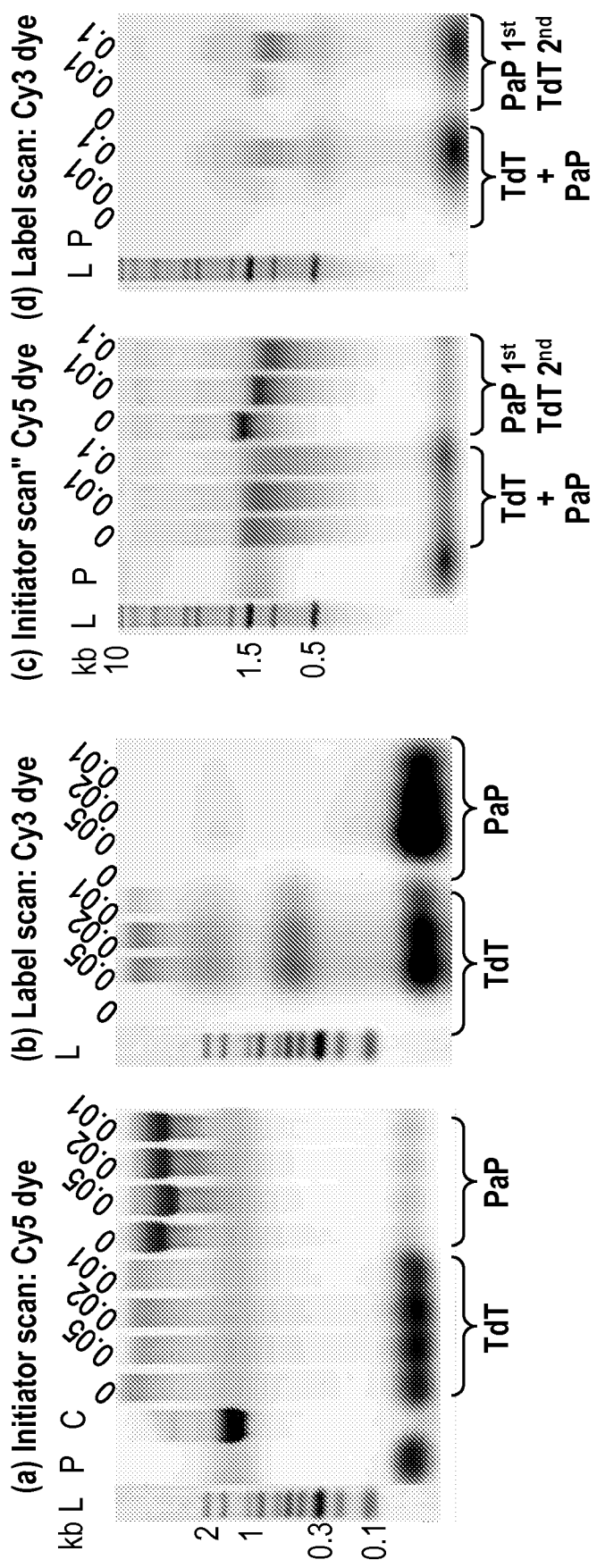
FIG. 2 shows electrophoretic gels containing e.g., RNA products, including Cy3-labeled products.

FIG. 2. Gel electrophoresis shows the extent of incorporation of Cy3-labeled nucleotides into the polymerized RNA product that is grown from the 3'-end of a short RNA primer by TdT, PaP, and a mixture of the two enzymes. A Cy5-tagged RNA (Cy5- rA15) is used as the primer (initiator) with ATP and Cy3-ATP (for PaP catalyzed polymerization) or dATP and Cy3-dATP (for TdT, or mixed TdT and PaP catalyzed polymerization) as monomers. Extended products are visualized by the appearance of higher MW bands in gels imaged at the Cy5 fluorescence emission wavelength due to labeling of the primer with Cy5 fluorophore (initiator scan), while the degree of incorporation of Cy3-labeled nucleotides are visualized in gels that are imaged at the Cy3 fluorescence emission wavelength (label scan). (a) Extent of RNA polymerization for the TdT and PaP catalyzed reactions; (b) incorporation of Cy3 nucleotides into polymerized product by TdT and PaP catalyzed reactions; (c) Extent of RNA polymerization for the by TdT and PaP in "one pot" and sequential PaP and TdT reactions; and (d) incorporation of Cy3-dATP in a "one pot" and sequential PaP, TdT reactions. The ratio of Cy3 labeled nucleotides and the corresponding natural nucleotides as monomers used in each reaction is indicated by the numbers on the top of each lane. Lanes "L", "P", "C" correspond to ssDNA ladder, RNA primer (no polymerization), and a positive control for the TdT catalyzed reaction, where a DNA primer was extended by TdT, respectively.

As shown in FIG. 2(a), Cy5-tagged RNA primers (Cy5-rA15) are a poor initiator for TdT catalyzed DNA polymerization, as seen by the presence of the majority of the RNA strands at the bottom of the gel, which corresponds to the original length of the RNA primer (lane P). This observation was expected because RNA is not the native substrate for TdT. Consequently, in a TdT reaction mixture that contains dATP and Cy3-dATP, the low reaction initiation efficiency results in a limited amount of Cy3-dATPs being incorporated into the extended chain, as indicated by the intense bands of unreacted Cy3-dATPs in FIG. 2(b). Consistent with this observation, a small fraction of the RNA primers serve as initiators for the polymerization of dATP as seen by presence of faint high MW, Cy5 labeled bands in the upper part of the gel in FIG. 2(a). In addition, the low level of Cy3-dATP incorporated in the product is visible in the gel scanned at the Cy3 emission wavelength in FIG. 2(b), which indicates that TdT can incorporate Cy3-dATPs into the extended polydA, from a short RNA primer, albeit with very low efficiency.

Example 9

RNA Labeling by RNA Polymerization Using PaP

Due to the inefficiency of TdT in recognizing a short RNA primer as an initiator, we investigated the ability of yeast PaP, a RNA polymerase, to catalyze the polymerization of RNA from an RNA primer with ribonucleotides (NTPs) as the monomer. Previous studies have shown that yeast PaP can incorporate various unnatural NTP analogs, such as the chain-terminating 3'-deoxy ATP, biotin-UTP, DIG-UTP, fluorescein-ATP, and aminoallyl-UTP. We examined the ability of yeast PaP to incorporate Cy3-ATP from a reaction mixture that also contains the native substrate—ATP—of PaP, recognizing that PaP is unlikely to catalyze polymerization solely using Cy3-ATP. As shown in the last four lanes of FIG. 2(a), wherein the gel was scanned at the emission wavelength of Cy5 (that labels the primer), PaP catalyzed polymerization is efficient as seen by the appearance of new high MW bands. However, the corresponding lanes in FIG. 2(b) show that these bands show virtually no Cy3 fluorescence, indicating that little Cy3-ATP is incorporated into the polyA that is polymerized by PAP. The lack of Cy3 labeling suggests that PaP has a strong preference for ATP as the substrate, so that Cy3-ATP is excluded from the polymerized chain. These results clearly indicate that using yeast PaP to incorporate fluorescent labels by polymerization of RNA is not likely to be a viable approach for the detection of RNA by SIEP.

Example 10

RNA Labeling by DNA Polymerization Using PaP and TdT

We found one report that yeast PaP could incorporate dATP at the 3'end of an RNA primer. We verified this finding by extending an RNA primer with PaP, using dATP as the monomer in the polymerization mixture. We found that RNA primers were modified with up to two dATP moieties at the 3'-OH terminus after a 2 h reaction. Although this process is clearly inefficient, it suggested an interesting solution to the conundrum of extending an RNA target efficiently while also incorporating fluorophores into the polymerized strand by using PAP to add a short oligo(dA) tail at the 3'-OH end of the RNA target, which could subsequently initiate DNA polymerization and incorporation of fluorescently labeled dNTPs by TdT.

We investigated this observation in more detail in two separate experiments where the reactions catalyzed by PaP and TdT were either carried out in "one-pot", or sequentially (PaP first, then TdT) using a Cy5-tagged RNA primer (Cy5-rA15), and a mixture of dATP and Cy3-dATP as the monomers. As shown in FIGS. 2(c) and 2(d), the sequential PaP and TdT reaction shows a higher primer extension efficiency and greater incorporation of Cy3-dATP in the polymerized ssDNA strand as compared to the one-pot reaction. More importantly, most of the input primer was extended in the sequential reaction of PaP followed by TdT. The extended product length was ~1-2 Kb, and is a function of the monomer (dATP) to initiator (RNA primer) ratios (M/I) in the reaction. We were also able to incorporate multiple fluorescent dNTPs in the extended product in the one-pot or sequential PaP and TdT reactions, which was not possible with PaP alone. Furthermore, in comparison between the one pot and sequential reactions of PaP and TdT, we obtained better overall efficiency in the sequential approach as seen by greater extension efficiency, longer and more uniformly sized products (FIG. 2(c)), and a higher degree of incorporation of Cy3-dATP (FIG. 2(d)).

We next compared the TdT alone, the "one-pot", and the sequential PaP and TdT catalyzed reactions by quantifying the efficiency of primer extension and the incorporation of Cy3-dATP in the polymerized product (FIG. 3). We included the reaction with TdT alone to demonstrate the necessity of using PaP with TdT combination to efficiently label RNA and generate signal amplification. The quantification excludes any unextended RNA primer or any RNA chain that is <20 bases in length, as well as unreacted monomers (dATP and Cy3-dATP). In terms of primer initiation efficiency, TdT alone only extended ~3-6% of the RNA primer, while in the "one-pot" PaP and TdT reaction, the percentage of primer extended was ~17-33% depending on the [Cy-3dATP]/[dATP] ratio. The sequential PaP and TdT catalyzed polymerization exhibited the highest efficiency, with polymerization initiated from ~50% of RNA primers at all [Cy-3dATP]/[dATP] ratios (FIG. 2(a)). We also measured the degree of labeling per polymerized ssDNA chain, by quantifying the number of Cy3-dATPs that were incorporated into the extended chain (FIG. 3(b)). Reaction with TdT alone resulted in the highest degree of labeling per extended chain, whereas the two enzyme methods exhibited fewer number of Cy3-dATP incorporated per chain, with the sequential reaction incorporating a higher number of Cy3 labels compared to the "one-pot" reaction.

Taking both the primer extension efficiency and number of fluorophores incorporated in each extended chain into account, and normalizing the total Cy3 signal by the amount of total initiator (input RNA primer) in each reaction, FIG. 2c shows the overall "effectiveness" of labeling for a given amount of RNA initiator. Clearly the sequential reaction is more efficient and generates greater degree of labeling, as indicated by the average of ~20 Cy3-dATP incorporated per RNA primer. These results clearly establish that the sequential reaction of PaP followed by TdT labeling is the optimum strategy for amplified direct labeling of RNA.

FIG. 3. Quantification of incorporation of Cy3-labeled nucleotides into the polymerized RNA product that is grown from the 3'-end of a short RNA primer by TdT, and by a mixture of TdT and PaP. A Cy5-tagged RNA primer (Cy5-rA15) was subjected to TdT, "one pot", or sequential PaP and TdT catalyzed reactions as a function of the molar ratio of Cy3-dATP to dATP ranging from 0.01 to 0.2. (a) The fraction of extended RNA primer, which represents the fraction of input primer that was extended to >20 base for the TdT, and TdT and PaP ("one-pot" and sequential) reactions as a function of the molar ratio of Cy3-dATP to dATP. (b) Number of Cy3 incorporated per extended chain as function of Cy3-dATP to dATP in polymerization mixture. (c) The average degree of labeling that accounts for the number of Cy3-dATP incorporated normalized to the amount of input primer in the reaction.

Example 11

Direct On-Chip Detection of Short and Long RNA Targets by SIEP Amplification

Figure 4A:
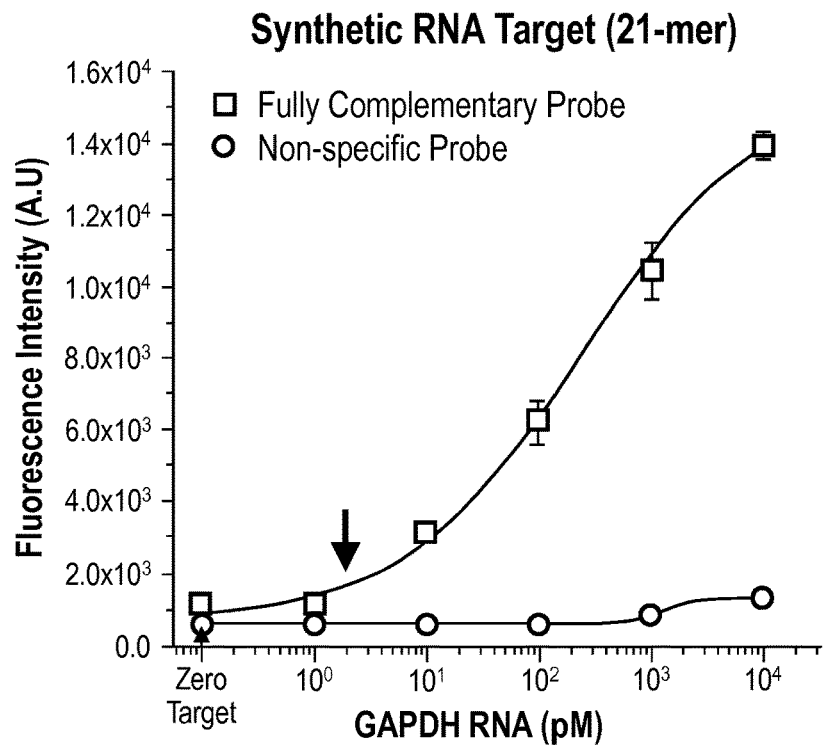
FIGS. 4(a), 4(b), and 4(c) show dose responses curves of RNA hybridization and successful detection of target RNAs.
Figure 4B:
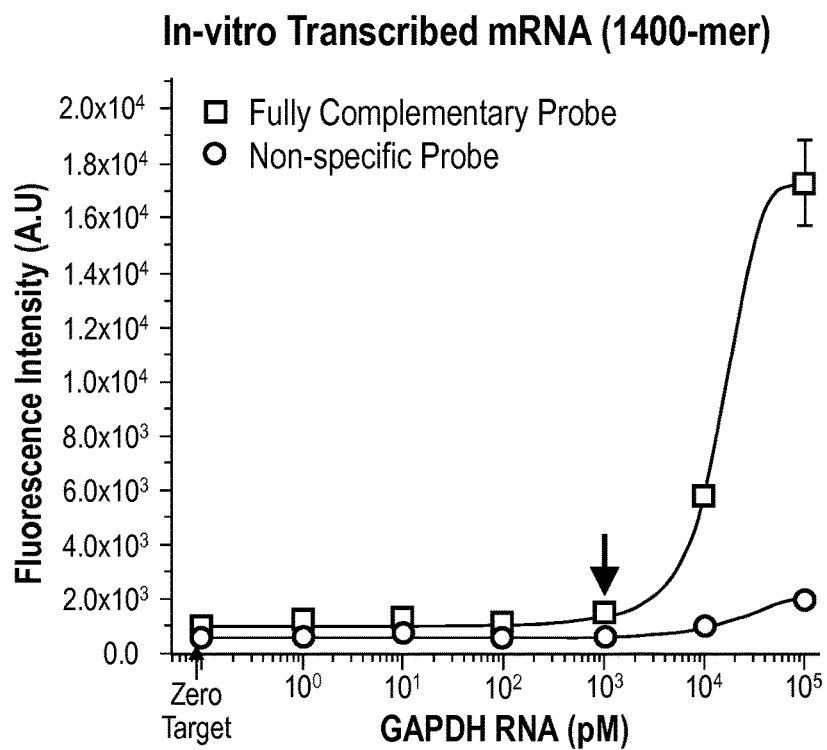
Figure 4C:
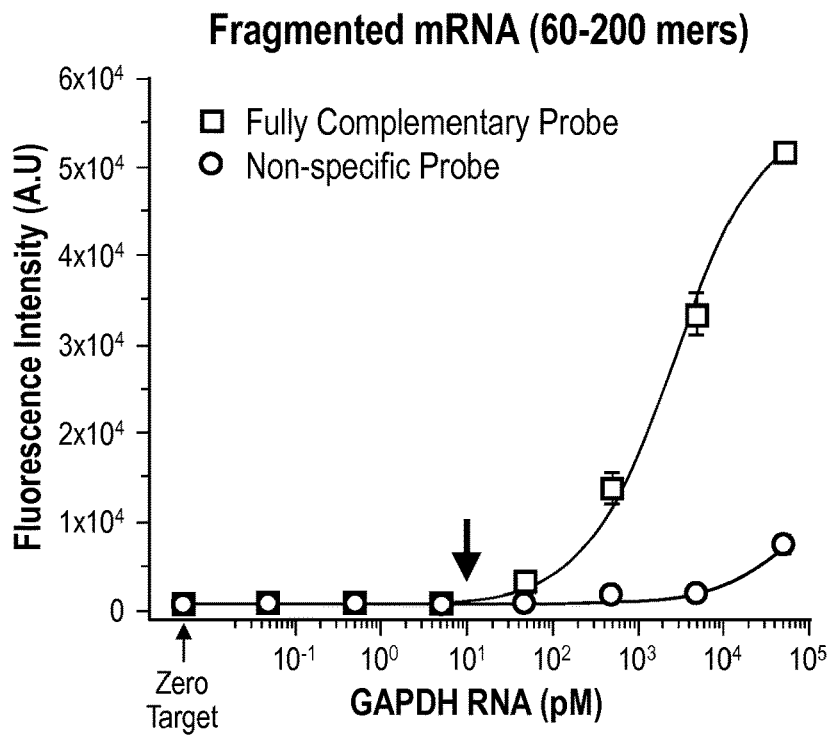
Figure 4D:
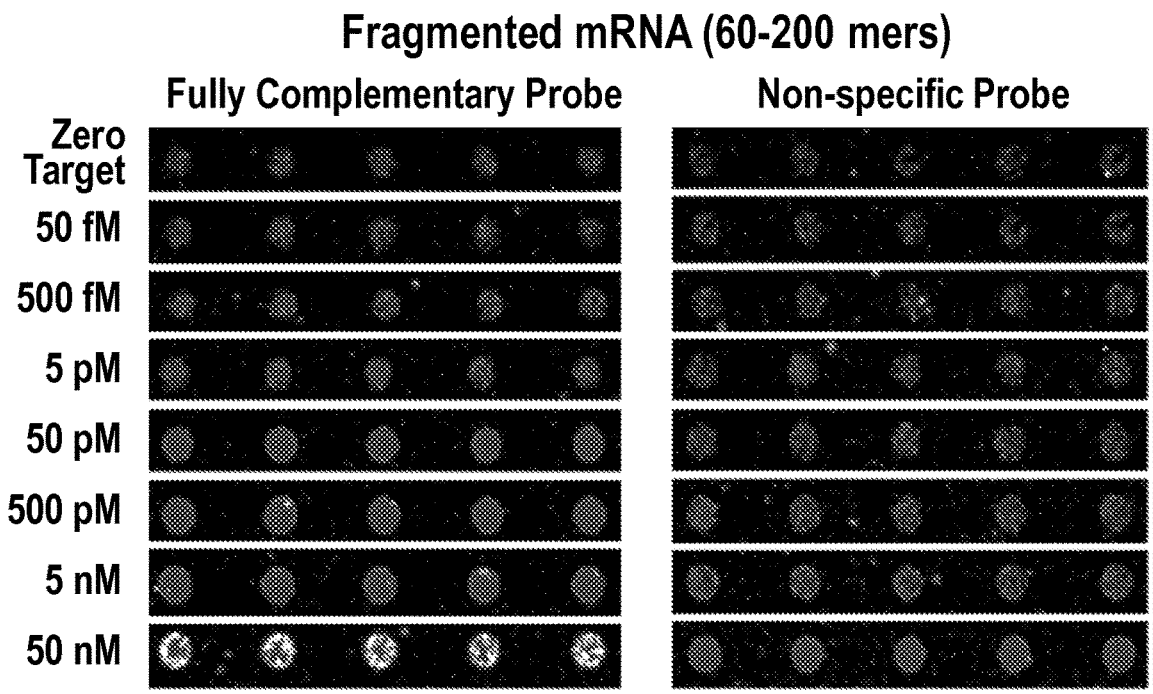
FIG. 4(d) shows limits of detection of the methods described herein.

Next, we evaluated the sequential PaP and TdT reaction for amplified on-chip fluorescence detection of RNA hybridization to a surface-bound probe. We chose PNA capture probes for their high affinity for RNA target and because they are not substrates for PaP or TdT, which eliminates the possibility of non-specific SIEP from the surface-bound probe. We printed the PNA probes on a "non-fouling" POEGMA slide because it prevents non-specific binding of biomolecules, and chose Cy5-dATP as the label by TdT catalyzed DNA polymerization because its fluorescence emission maximum is in the far-red region, which avoids any auto-fluorescence signals from the glass slide. We obtained dose-response curves for short and long RNA targets (FIGS. 4a and 4b, respectively). For a short 21 base long synthetic RNA target that has the same length as most miRNA (FIG. 4a), the LOD was ~2 pM. This LOD corresponds to 0.16 fmol target in an 80 µL hybridization buffer, which is comparable to previously reported LOD for unamplified samples on other array platforms for short RNA targets such as miRNA and is similar to the LOD for DNA detection using TdT reported by us previously. See, Tjong et al., Analytical Chemistry. 2011. 83(13), 5153-5159.

We next investigated the direct detection of a full-length mRNA target with a 17 base complementary sequence for a surface-bound PNA probe. The LOD of a long 1.4 Kb RNA target was 1 nM, which is 3 orders of magnitude larger as compared to the short RNA target (FIG. 4). The source for the decline in performance is largely due to the long target mRNA molecule. This observation is consistent with other studies reported in the literature, where large nucleic acid targets (cDNA or mRNA) reduce the sensitivity and specificity of microarray analysis.

There are several possible reasons for this lower LOD. First, in all surface based assays, including microarrays printed on a surface, diffusion of the targets to the surface-immobilized probes could be a limiting step. For a typical microarray assay, hybridization of mRNA target is carried out with mild fluid agitation/rotation in a reaction chamber. Thus at low target concentration, hybridization occurs in the mass transport limited regime and the diffusive flux of the target molecules is the rate limiting step that governs the capture of the probe by the target. In the diffusion-limited regime, the steady-state accumulation of target molecules on the probe spot is proportional to the diffusion coefficient (D) of the target. We calculated that D for the 21 base long RNA is $1.4 \times 10^{-10}$ m$^2$/s, while for a 1.4 Kb RNA, D is estimated to be $7.7 \times 10^{-12}$ m$^2$/s using a reported diffusion coefficient for a reference 7.5 Kb RNA39 and a scaling rule for DNA diffusion coefficients on a similar length scale. The lower D for 1.4 Kb RNA decreases the detection sensitivity of long target mRNA molecules. In addition, the target region in the 1.4 Kb RNA may be buried within self-complementary secondary structures, thus making it less accessible for hybridization. Furthermore, once hybridized to the probe, hydrodynamic drag on the free hanging strands may disrupt the hybrid that is only 17 bp long. Finally, after target is hybridized to the probes, the secondary structure of a long RNA may hinder SIEP, due to inaccessibility of the 3'-OH end that acts as the initiation site for SIEP.

FIG. 4. Dose-response curves of RNA hybridization shows successful on-chip fluorescence detection by SIEP of a short synthetic 21 base long RNA target (a), a full length 1.4 Kb long mRNA target (b), and a fragmented mRNA target (c). Improved detection sensitivity for 1.4 Kb long RNA by fragmentation and on-chip phosphatase end-repair is demonstrated in (c). The image of the probes with labeled bound mRNA fragments is shown in (d). Arrows indicate the LOD (limit of detection) as determined by the target concentration at signal from no target control plus 3× standard deviation.

Example 12

RNA Fragmentation and End-Repair for Improved Detection Limit for Long mRNA Targets We attempted to improve the sensitivity of mRNA detection by carrying out an RNA fragmentation step, a method that is known to increase the detection sensitivity of long targets. Although there are other solutions to relieve problems associated with the detection of long mRNA, such targeting the mRNA to the probe by electrostatic or magnetic fields, by pumping the fluid sample past the sensor, by using a special fluid chamber geometry, and by employing 3D hierarchical microsensors with nanoscale features to enhance probe display, fragmentation of long targets is the most straightforward approach while maintaining the simplicity of our assay without major modifications to our processing steps. The benefits of RNA fragmentation are: (1) by breaking a long target into small fragments, the rate of diffusion of the fragment that bears the target sequence is dramatically enhanced; (2) target sequence on small fragments are more accessible to surface-bound probes and more likely to stay attached to the surface during labeling by SIEP; (3) the 3'-OH in small fragments is more accessible for labeling by PaP and TdT as compared to a longer target.

Figure 13:
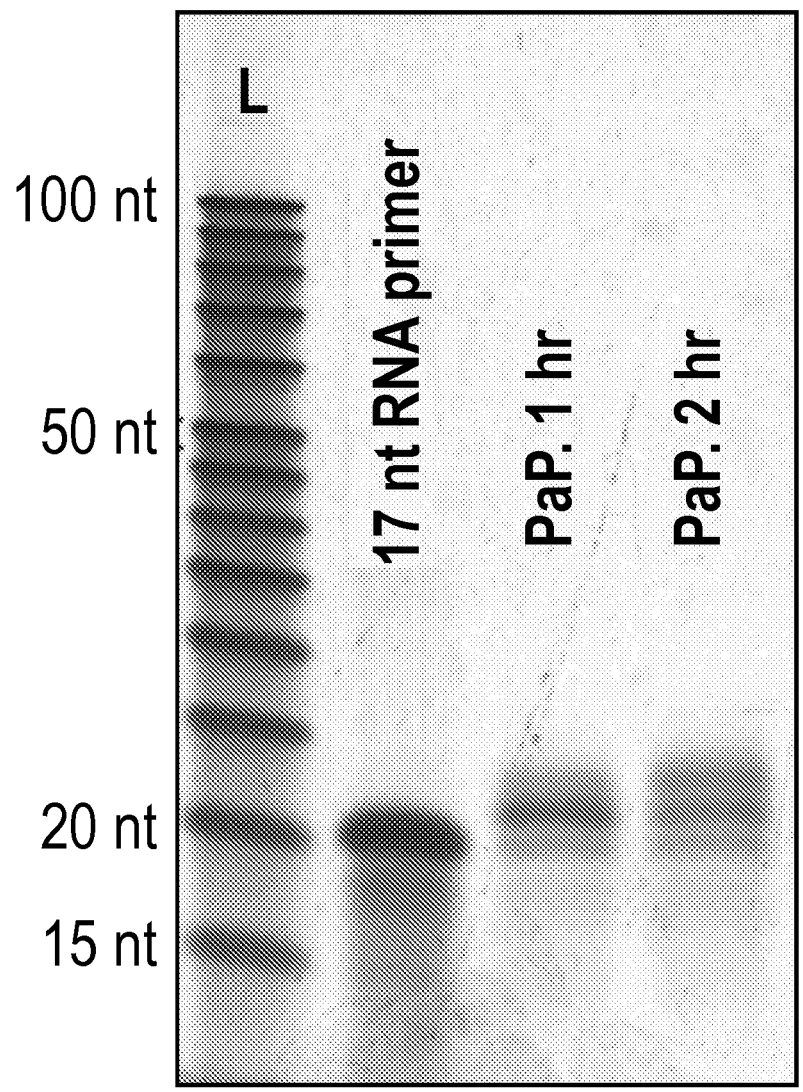
FIG. 13 demonstrates the incorporation of dATP into an RNA primer by PaP.

We carried out standard Zn-mediated RNA hydrolysis using commercially available reagents and protocols (Ambion), which cleaves long RNA molecules into 60-200 nucleotide fragments in less than 20 min. The RNA fragments resulting from this cleavage primarily contain a 3'-phosphate group as opposed to the desired 3'-OH group necessary for polymerization by PaP or TdT. We hence devised an additional end-repair step by phosphatase treatment following fragmentation to remove the 3'-phosphate and recover the 3'-OH. We used Antarctic Phosphatase for this purpose and carried out an experiment in solution to verify the repair step. The gel electrophoresis of fragmented mRNA target, with and without phosphatase treatment showed that phosphatase repair greatly improves the PaP and TdT reaction initiation efficiency and hence incorporation of Cy3-dATP (FIG. 13).

After fragmenting the 1.4 Kb long GAPDH mRNA followed by on-chip 3'-end-repair by phosphatase, we carried out a sequential PaP and TdT catalyzed polymerization using a mixture of dATP and Cy3-dATP as the monomers, as described previously. We obtained a 10 pM LOD for fragmented and end-repaired full length mRNA input (FIG. 4c), which is a 100 fold improvement from the 1 nM LOD for the full-length mRNA and similar to the LOD obtained for the short, synthetic RNA target (FIG. 4a). The additional step of mRNA fragmentation and on-chip phosphatase repair are easy to perform using established protocols and commercially available reagents, so that they do not significantly increase the complexity of the assay.

Example 13

Multiplexed RNA Detection

Figure 5A:
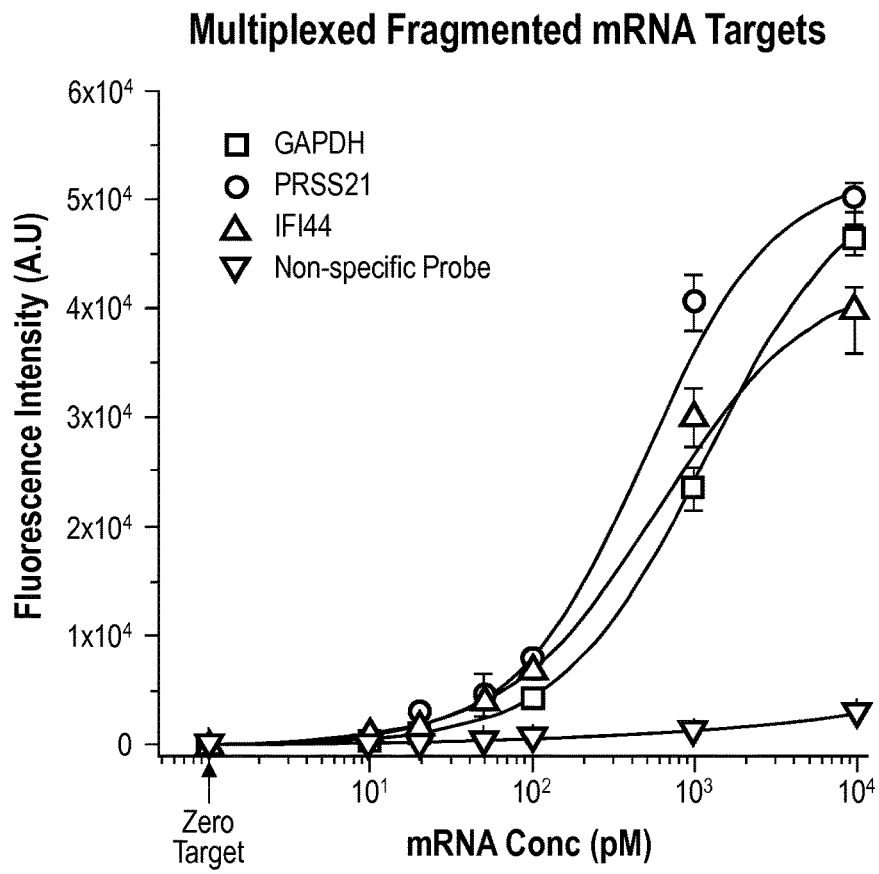
FIGS. 5(a) and 5(b) show sensitivity and specificity of polynucleotide probes and fluorescence detection for different target RNAs.
Figure 5B:
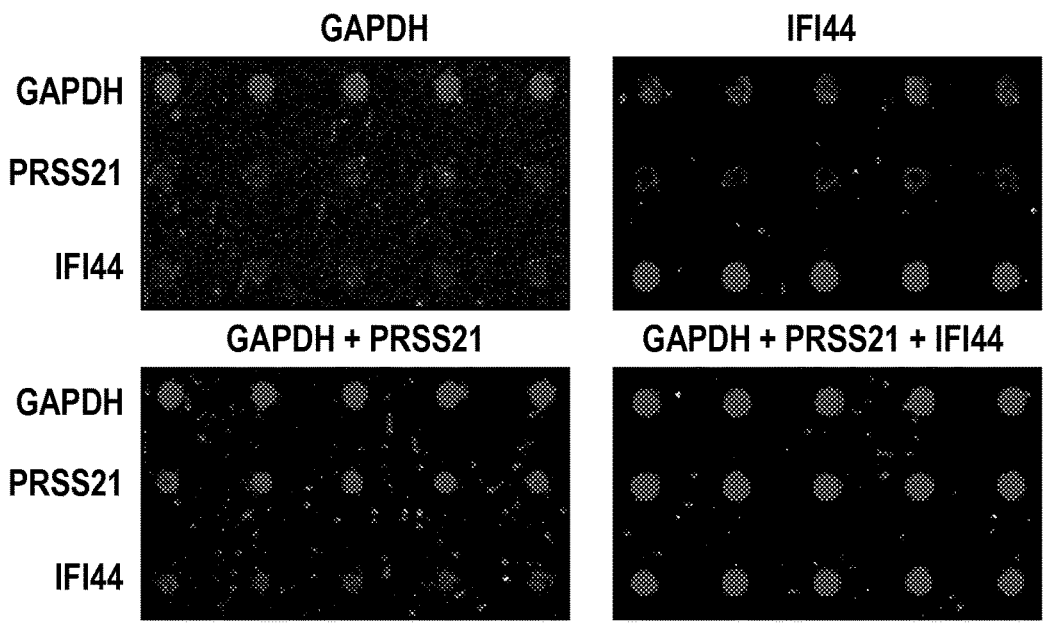

With these results in hand, we investigated the potential of SIEP to detect multiple mRNA targets in a microarray format. We were also interested in examining whether this assay would be immune to sequence dependent bias, which is critical for quantitative and robust multiplexed detection. To do so, we performed a microarray analysis of a mixture of mRNA target molecules consisting of full length GAPDH, PRSS21, and IFI44 mRNA transcripts that were fragmented, and then captured by probes that were spotted on POEGMA-coated glass slides, followed by fluorescence detection by sequential TdT and PaP catalyzed SIEP. As shown in FIG. 5a, we can detect individual fragmented mRNA target in a mixture and maintain the sensitivity for the assay at ~10 pM for all targets, suggesting that the presence of three targets simultaneously does not degrade the sensitivity of the assay given the large number of short RNA strands generated by the fragmentation of the three full-length mRNA transcripts. A control probe that is non-complementary to any of the fragments generated from the mRNA transcripts was also used in the assay, and showed a near flat dose-response curve with low signal, demonstrating that non-specific SIEP in the absence of hybridization of the target to its probe is minimal. Control experiments were also performed in which one or more of the targets were omitted from the hybridization mixture to confirm the specificity of the assay (FIG. 5b). FIG. 5. The sensitivity and specificity of the probes and fluorescence detection by SIEP are demonstrated by multiplexed detection of three mRNA transcripts. In (a), the dose-response curves of fragmented in vitro transcribed GAPDH, PRSS21, and IFI44 genes, analyzed simultaneously in heterogeneous mixture samples, has an LOD of 10 pM and in (b), specificity of the assay is demonstrated with a 100 pM target when individual targets or a mixture of targets are exposed to the microarray.

Example 14

Converting RNA to DNA Via dATP Tailing Using PaP

We examined the incorporation of dATP into a 17 nt long RNA primer (termed "initiator") [5'-rGrCrA rArCrA rGrGrG rUrGrG rUrGrG rArC-3'] (SEQ ID NO: 6) using yeast PaP by reacting excess dATP monomer with RNA primer (monomer/initiator ratio M/I=200). We found that the majority of RNA primers were modified with dATP at the 3'-OH terminus, as indicated by the appearance of extra bands with higher molecular weight on the denaturing polyacrylamide gel (FIG. 13). The gel is able to resolve molecules with single nucleotide difference, which enabled verification of the addition of dATP into the RNA primer. However, as shown in FIG. 13, even after 2 h PaP reaction, only limited incorporation of dATP is observed due to the slow kinetics of dATP polymerization by PaP. We observed a 2 nucleotides extension after 2 hr reaction, with a small amount of RNA primers that remained unextended (FIG. 13).

Example 15

Labeling of Fragmented mRNA

Figure 14:
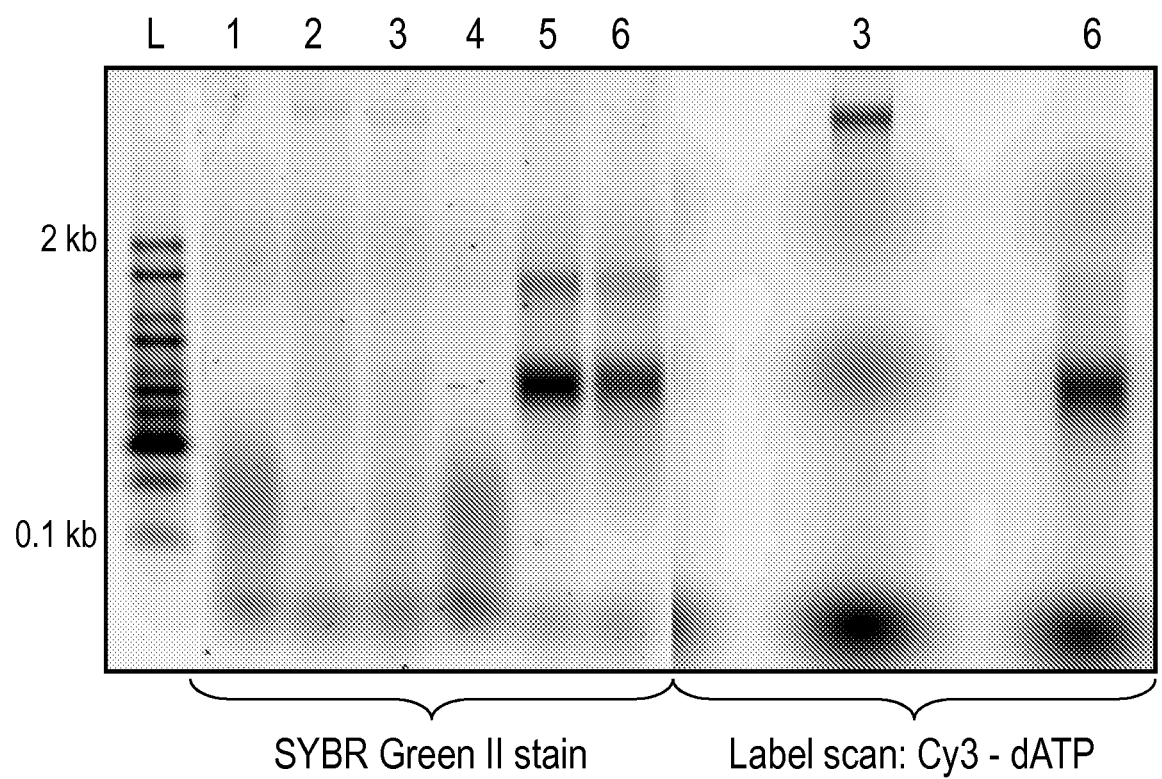
FIG. 14 shows the effects of phosphatase treatment of fragmented mRNA undergoing sequential PaP and TdT fluorometric labeling.

We compared phosphatase treated and untreated fragments for the PaP and TdT sequential labeling by reacting purified fragmented mRNA with (1) dATP only and (2) in a reaction mixture containing Cy3-dATP and dATP at a 0.5 molar ratio of Cy3-dATP/dATP. As shown in FIG. 14, phosphatase treatment of fragmented mRNA samples did not affect sample integrity (lane 1: untreated and lane 4: phosphatase treated). In addition, Sybr Green II stain clearly showed that fragmented mRNA without phosphatase end-repair was inefficiently extended, with a broad distribution of products (lane 2 and 3) while the fragments that were treated with phosphatase were efficiently extended and resulted in a more uniform extension product with two major bands (lane 5 and 6). Furthermore, the majority of extended products were successfully labeled with Cy3-dATP (lane 6, in the label scan image). Although some untreated fragments were extended (lane 2 and 3) and labeled with Cy3-dATP (lane 3, label scan image), this only occurred in a small fraction of the fragmented samples. This experiment verified the need to end-repair the fragmented mRNA for efficient labeling of RNA molecules using PaP and TdT.

FIG. 14. Gel electrophoresis of fragmented mRNA, phosphatase treated (lane 4-6) and untreated (lane 1-3), undergoing PaP and TdT sequential labeling. SYBR Green II stain shows the unextended (lane 1 and 4) and extended products (lane 2-3 and 5-6) while Cy3 scan shows extended product with incorporated Cy3-dATP (lane 3 and 6). Lane L represents the RNA ladder.

Example 16

Figure 15:
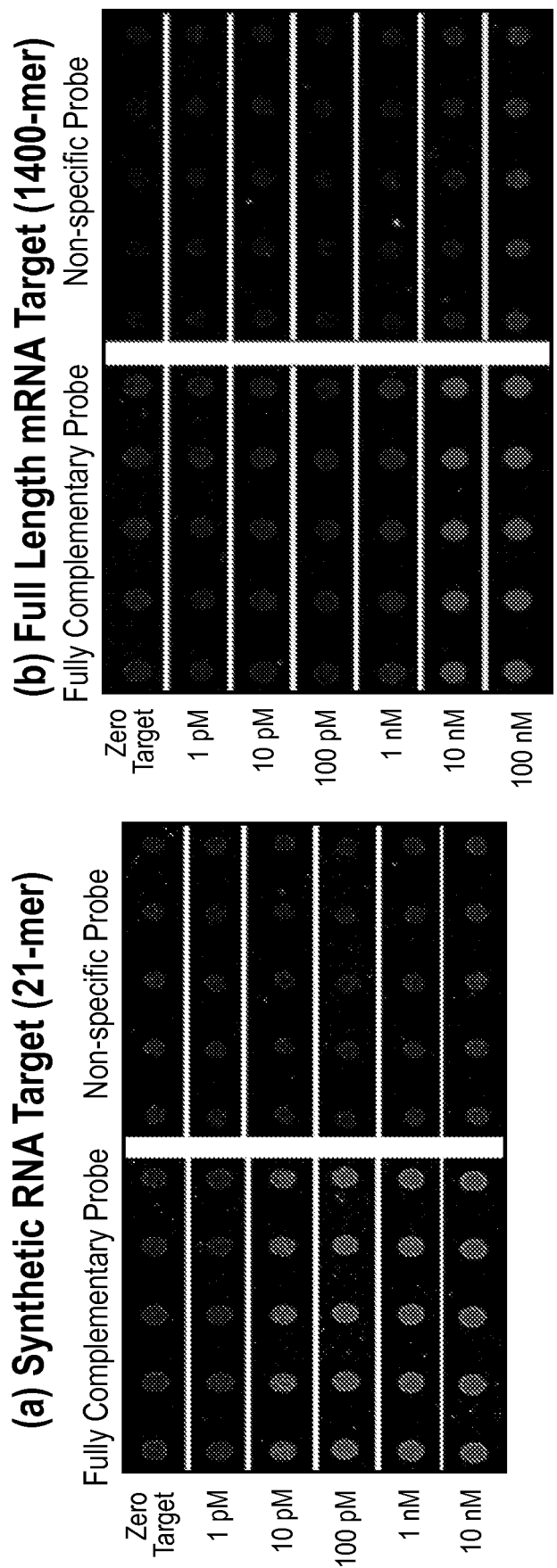
FIG. 15 shows microarray images of printed PNA probes that have been incubated with (a) 21-mer target or (b) a 1400 bp long in vitro transcribed mRNA and labeled with fluorescent nucleotides by sequential PaP and TdT reactions.

Direct Detection of Short and Long Strands of RNA Target Via On-Chip SIEP Amplification We show the fluorescent intensity of the PNA probe spots in FIG. 15 as a supplement of the dose-response curve plotted in FIGS. 3a and 3b. The increase in the fluorescence signal as the target concentration increases can be discerned clearly, and the better sensitivity achieved by hybridization of shorter target compared to full-length mRNA transcripis is evident by comparing FIGS. 15a and 15b.

FIG. 15. Microarray images of printed PNA probes incubated with their fully complementary complementary targets: a short 21 nt long target in (a) and 1400 nt long in vitro transcribed mRNA in (b). Labeling was carried out by sequential PaP and TdT SIEP.

Formation of an Annealed, Extended Target Nucleic Acid, Formation of a Metal Complex of the Annealed, Extended Target Nucleic Acid with Metal Nano-Particles, and Detection of the Complex Example 17

Uses of Metallic Nanoparticles

The use of gold nano particles (AuNPs) for DNA detection has been largely in the form of a tag. Generally, the DNA target is labeled with AuNPs through affinity tag (biotin-streptavidin, antibody) (Liang et al. 2005; Suzuki et al. 2006) or a detection probe that can recognize the targets and are labeled with AuNPs. (Bao et al. 2005; He et al. 2000; Storhoff et al. 1998; Taton et al. 2000)_ENREF_1 Although this strategy has been successful, the need for affinity tag labeling on the target, designing a probe, and exposure to the detection probes introduce additional complexity in the assay. To simplify the assay, several strategies that can interrogate DNA target directly have been developed, particularly by exploiting the polyelectrolyte property of a DNA molecule, the electrostatic interaction of AuNPs and a polyelectrolyte, or charge screening phenomenon. (Kanjanawarut and Su 2009; Kim et al. 2010; Li and Rothberg 2004; Xia et al. 2010) For example, Kim et al. (Kim et al. 2010) immobilized PNA probes to hybridize with DNA target which subsequently detected by positively charged AuNPs. Due to the electrostatic interactions, the AuNPs selectively attach to the hybridized, negatively charged DNA, which can be visualized by the naked eye or an optical flatbed scanner after the treatment with metal enhancement solution.

Our strategy is very similar in the way that we exploit the electrostatic interactions between the negatively charged DNA phosphate backbone and the positively charged AuNPs. However, in order to increase the net negative charge on the hybridized target, we applied our unique SIEP technology as an on-chip signal amplification method. We demonstrate that SIEP improves the sensitivity and the selectivity of the colorimetric assay by simply adding a one step, post-hybridization, and isothermal reaction. Overall, amplified colorimetric SIEP assay has all the positive attributes of SIEP assay (Tjong et al. 2013; Tjong et al. 2011) and in addition the ability to assess hybridization of DNA or RNA target visually without the need for fluorescent microscope or scanner.

Example 18

Study Materials

All oligonucleotide primers and targets used in this study were synthesized by Integrated DNA Technologies, Inc, while the PNA probes were synthesized by Panagene. TdT enzyme, TdT buffer, and dNTP monomers (dATP and dTTP) were purchased from Promega while ATP monomer, yeast PaP, and buffer were supplied by Fermentas and Affymetrix. Chemicals for nanoparticles synthesis and gold enhancement such as chloroauric acid (HAuCl4), cetyltrimethylammonium bromide (CTAB), sodium borohydride (NaBH4), phosphate buffer (PBS), Tween 20, polyethyleneimine (PEI, branched, Mw: 25,000), potassium thiocyanate (KSCN), postassium gold (III) chloride (KAuCl4), and hydroquinone were purchased from Sigma-Aldrich while sodium chloride and citric acid were purchased from EMD Chemicals, Inc. Gold nanoparticles, 1.4 nm positively charge particles, 5 nm thiol-PEG-amine modified, and 10 nm, 20 nm, 50 nm citrate stabilized particles were purchased from Nanoprobes, Inc, Nanocs, and Ted Pella, respectively. The nonfouling poly (oligo(ethylene glycol) methacrylate) (POEGMA) brush substrate for DNA primer and PNA probe immobilization were supplied by Mr. Angus Hucknall and made in-house following protocols previously described (Hucknall et al. 2009a) while streptavidin for anchoring the DNA and PNA probe were purchased from Sigma.

Example 19

Feasibility Study and Optimization of SIEP Colorimetric Assay

The DNA primers [1 μM of 5'-CGG GCA ACA TAC CTT-biotin-3'(negative control), 5'-biotin-dA10-3', and 5'-biotin-dT25-3'] (DNA sequence shown in SEQ ID NO: 7) and PNA primers [5'-Ac— CGG GCA ACA TAC CTT-lysine-biotin-3' (negative control)] (DNA sequence shown in SEQ ID NO: 8) were individually mixed with streptavidin (2 μM) and then spotted using a non-contact printer (Piezzorray, Perkin Elmer) on a nonfouling poly(oligo(ethylene glycol) methacrylate) (POEGMA) brush(Hucknall et al. 2009a; Hucknall et al. 2009b)_ENREF_18 grown on a glass substrate. The slides spotted with the primers were then incubated overnight in a vacuum chamber and then rinsed with 1×SSC buffer containing 0.1% Tween 20 before exposure to SIEP reaction at 37° C. for 1 h. SIEP reaction comprised of 10 U of TdT and dATP or dTTP monomers (0.1 mM, 0.5 mM, or 1 mM) in 100 IAL, of TdT buffer (1×, 100 mM potassium cacodylate, 1 mM CoC12, and 0.2 mM DTT, 0.1% Tween 20, pH 7.2). The slides were then rinsed three times with 1×SSC buffer with 0.1% Tween 20. Following STEP reaction, the slide were exposed to various sizes of positively charged gold nanoparticles (1.4 30 nm, 5 nm, 10 nm, 20 nm, and 50 nm) for 30 min and then rinsed three times with PBST buffer (1×PBS+0.1% Tween 20) before exposure to the gold enhancement solution for 4-7 min.

Example 20

Colorimetric SIEP Assay for Hybridization of DNA Target

The fully complementary PNA probe [1 µM, 5'-Ac-CAA TGC CAG CCC CAG CG-lysine-biotin-3'] (DNA sequence shown in SEQ ID NO: 9) and non-specific PNA probe [1 µM, 5'-Ac-GTT GCT GGT AGT TTA TG-5 lysine-biotin-3'] (DNA sequence shown in SEQ ID NO: 10) were individually mixed with streptavidin (2 µM) and then spotted using a non-contact printer (Piezzorray, Perkin Elmer) on a glass slide coated with a non-fouling polymer brush. The slide spotted with the primers was then incubated overnight in a vacuum chamber and then rinsed with 1× SSC buffer containing 0.1% Tween 20 before exposure to the DNA target. A dose-response curve of the hybridized target was generated by incubating the printed probes to a range of target DNA concentrations [1 pM-1 µM, 5'-CGC TGG GGC TGG CAT TGC CCT C-3'] (DNA sequence shown in SEQ ID NO: 11) for 4 h at 42° C. in 3×SSC buffer. After rinsing three times (1×SSC+0.1% Tween 20), the slide was exposed to STEP reaction using TdT to grow polydA (0.1 U/µ 1 TdT, 0.1 mM dATP in 1× TdT buffer) for 1 h at 37° C. The slides was then rinsed three times in 1×SSC buffer with 0.1% Tween 20 followed by another set of rinse in PBST. For gold nanoparticles labeling, the slides was exposed to 5 nm CTAB stabilized particles for 30 min. After three times rinsing in PBST, the slide was exposed to gold enhancement solution for 5 min.

Example 21

Colorimetric SIEP Assay for Hybridization of RNA Target

The fully complementary PNA probe [1 µM, 5'-Ac— CAA TGC CAG CCC CAG CG-lysine-biotin-3'] (SEQ ID NO: 9) and non-specific PNA probe [1 µM, 5'-Ac— GTT GCT GGT AGT TTA TG-lysine-biotin-3'] (SEQ ID NO: 10) were individually mixed with streptavidin (2 µM) and then spotted using a non-contact printer (Piezzorray, Perkin Elmer) on a glass slide coated with non-fouling polymer brush. The slide spotted with the primers was then incubated overnight in a vacuum chamber and rinsed with 1×SSC buffer containing 0.1% Tween 20 before exposure to DNA target. A dose-response curve of hybridized target was generated by incubating the printed probes to a range of target RNA concentrations [1 pM-1 µM, 5'-UUU GAC GCU GGG GCU GGC AUU GCC CUC-3'] (SEQ ID NO: 12) for 4 h at 42° C. in 3×SSC and 4.95 M urea buffer. After rinsing three times (1×SSC+0.1% Tween 20), the slide was exposed to STEP reaction using yeast PaP to grow polyA (6 U/µ 1 PaP, 0.1 mM ATP in 1× PaP buffer) for 1 h at 37° C. The slides was then rinsed three times in 1×SSC buffer with 0.1% Tween 20 followed by another set of rinse in PBST. For gold nanoparticles labeling, the slides was exposed to 5 nm CTAB stabilized particles for 30 min. After rinsing three times in PBST, the slide was exposed to gold enhancement solution for 5 min.

Example 22

SIEP Amplification with Electrostatic Binding of AuNPs and DNA

Figure 6:
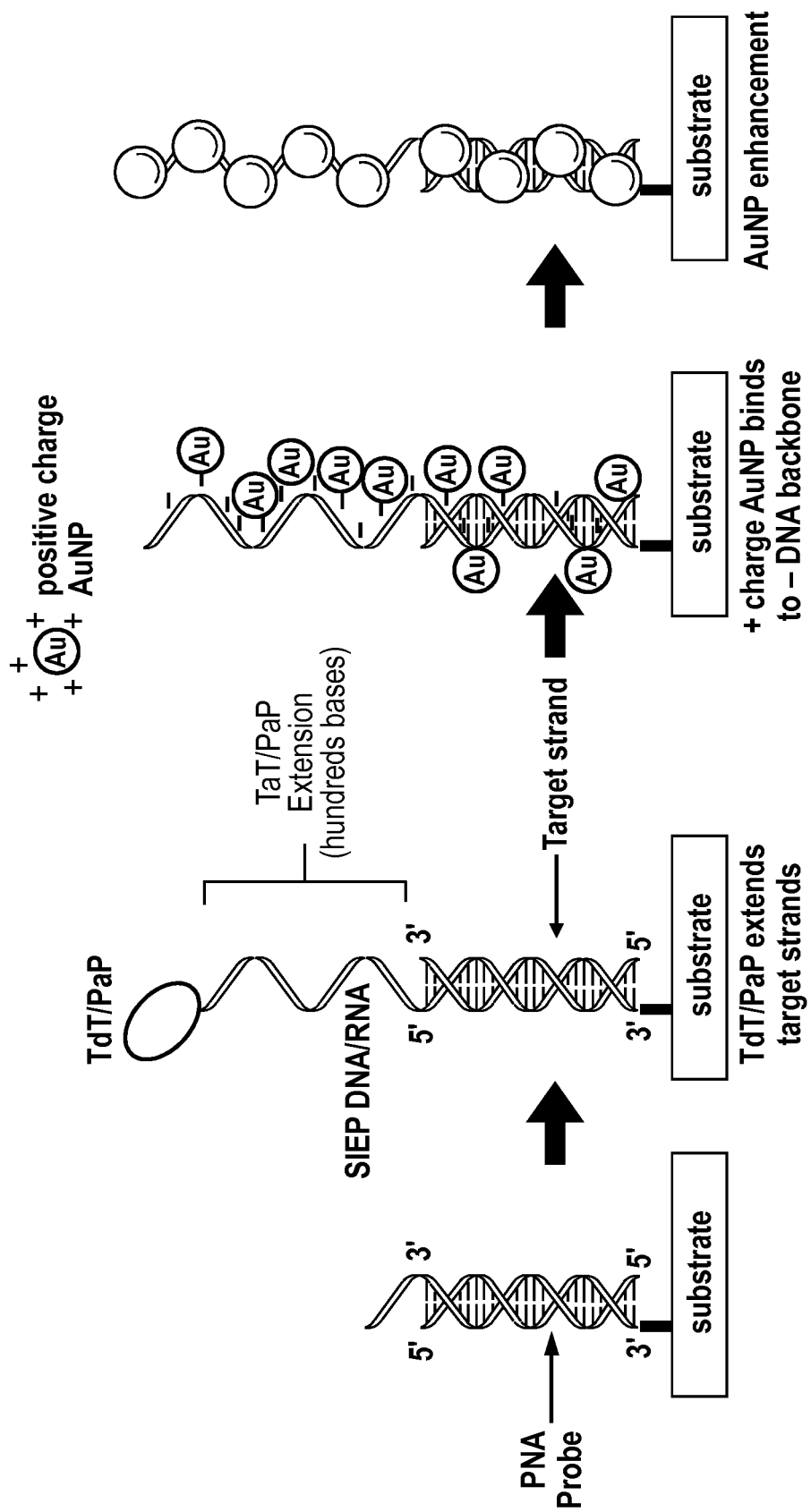
FIG. 6 shows formation of a complex comprising i) positively charged gold nano particles and ii) a polynucleotide probe annealed, extended RNA-DNA hybrid.

We verified our hypothesis on the use of SIEP as a signal amplification method and the electrostatic binding between positively charged AuNPs and DNA backbone for colorimetric assay (FIG. 6) by immobilizing PNA and DNA molecules with the 5'-end or the 3'-end exposed on a POEGMA polymer brush substrate (Hucknall et al. 2009a; Hucknall et al. 2009b)_ENREF_31 grown on a glass substrate. We selected PNA (17-mer) as a negative control due to its neutral peptide backbone so that to verify the selectivity of SIEP and AuNPs labeling towards DNA. We also included a negative DNA control for SIEP by immobilizing DNA molecules at their 3'-end, precluding any SIEP reactions on them and two positive DNA controls, 8 Kb DNA molecules (extended with TdT in solution) and DNA molecules immobilized at their 5'-end, exposing the 3'-OH end for SIEP reaction. In addition, we are interested to see if there is a difference between 5 nm and 10 nm (in diameter) AuNPs on the intensity of metallization spots they produced.

Figure 7A:
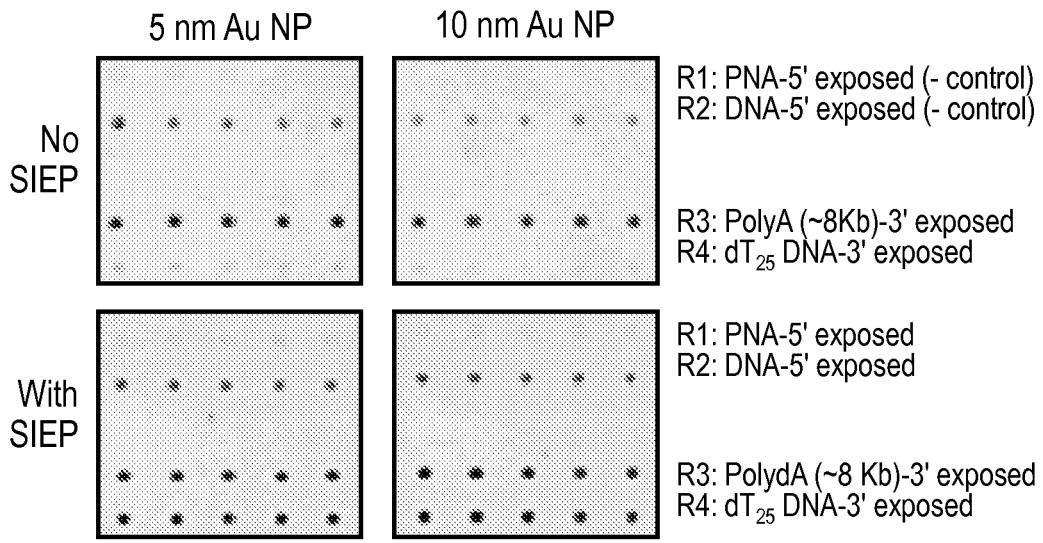
FIG. 7(a) shows flatbed scanner images of immobilized PNA and DNA spots with and without SIEP amplification after exposure to AuNPs and gold enhancement.

FIG. 7(a) shows the flatbed scanned image of the glass slide on which DNA is immobilized after 30 min AuNPs exposure and a few minutes of the gold enhancement step. Without SIEP reaction, no metallization spots appear on the row with PNA spots (R1), which verifies the selectivity of positively charged AuNPs towards DNA. FIG. 7(a) also shows that metallization is proportional to the length of DNA molecules as the highest intensity without SIEP reaction is generated on the row with 8 Kb polydA spots (R3). On the other hand, after 1 hr SIEP reaction, only faint metallized spots develop on the PNA row due to non-specific binding of AuNPs, while a drastic change in the intensity of dT25 spots appears (R4), which has the 3'-OH end exposed for SIEP extension. The intensity of the negative control DNA spots (R2) remains the same even after SIEP reaction because the exposed 5'end is unreactive towards SIEP extension, indicating that only limited non-specific AuNPs bind to the immobilized short DNA strand (15-mer). As for the 8 Kb polydA spots (R3), after SIEP reaction, there is a slight increase in their intensity. This increase could be due to limited SIEP extension because the 3'-OH might be buried due to the extremely long DNA chain adsorption onto the substrate. As for the different nanoparticles size tested in this experiment, similar intensities are produced by spots exposed to 5 nm and 10 nm AuNPs.

Figure 7B:
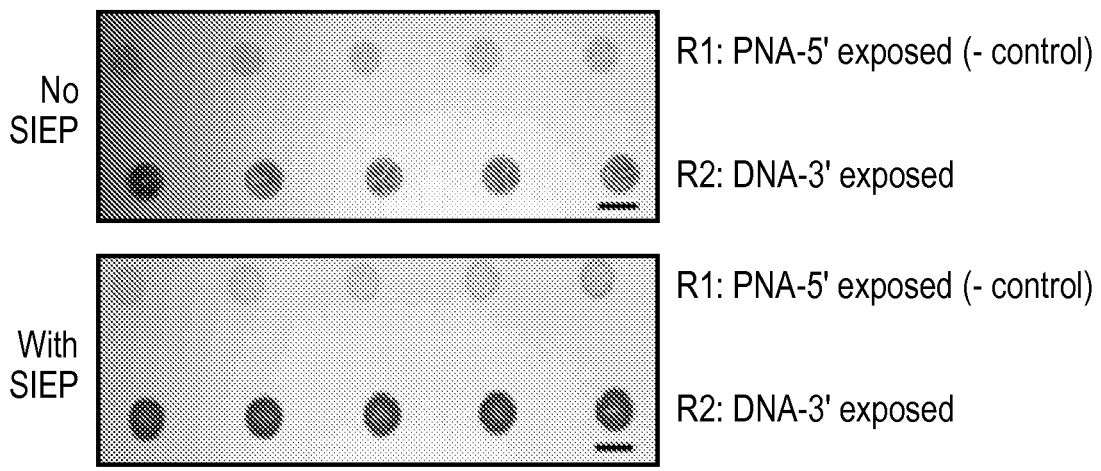
FIG. 7(b) shows an optical microscope image of DNA spots, with and without SIEP after AuNP enhancement, showing morphology of developed metallized spots (scale bar 150 μm).

A further investigation on the morphology of unextended PNA and extended DNA spots were carried out by imaging the substrate with an optical microscope. As shown in FIG. 7(b), marked differences in the metal deposition can be observed before and after the SIEP reaction, especially on the negatively charged DNA. This result validates that the SIEP reaction does extend DNA with 3'-OH exposed on the surface and that the AuNPs is positively charged, is able to bind electrostatically to the negatively charged DNA phosphate backbone, and the amount of AuNPs bound is proportional to the length of ssDNA chain.

Example 23

Colorimetric Assay Optimization

We studied several important parameters in the development of SIEP colorimetric assay; they are the size of the nanoparticles; the type of the monomer used in SIEP extension and the monomer concentration in SIEP reaction; the surface functionalization to impart positive charges on the AuNPs; and the gold enhancement solution that produce minimal non-specific metal deposition. Our objective is to study the nanoparticles interaction with surface immobilized long ssDNA and then establish a protocol that allows high sensitivity and selectivity for colorimetric detection, with SIEP amplification. The details on the assay optimization studies can be found in the supporting information (SI).

FIG. 7(a) Flatbed scanner images of immobilized PNA and DNA spots with and without SIEP amplification after exposure to AuNPs and gold enhancement. FIG. 7(b) Optical microscope image of DNA spots, with and without SIEP after AuNPs enhancement, showing morphology of developed metallized spots (scale bar 150 μm).

Example 24

Colorimetric Detection of DNA and RNA Hybridization by SIEP

We have established that SIEP colorimetric assay is feasible using positively charged AuNPs followed by the gold enhancement step. Using optimized protocol (see SI) that comprised of dATP for SIEP polymerization, ~5 nm CTAB modified AuNPs as seeds for metallization, and in-house developed gold enhancement solution, we generated dose response curves for DNA and RNA target, using PNA as the capture probe.

Example 25

Dose Response Curve of DNA Target Hybridization

We assessed SIEP colorimetric assay for the analysis of DNA targets by hybridizing 22-mer DNA targets onto immobilized PNA probes on a POEGMA polymer brush substrate. The hybridized targets were then exposed to TdT reaction containing 0.1 mM dATP for 1 hr at 37° C., selectively polymerizing dATP from the 3'-OH of bound target. The SIEP amplified target was then exposed to positively charged AuNPs (~5 nm in diameter, CTAB modified) for 30 min. After rigorous rinsing, gold enhancement step was carried out for 5 min. The substrate with metallized DNA spots was then spun dry and imaged with a flatbed scanner for intensity analysis and an optical microscope for detailed morphology.

As shown in FIG. 8, hybridized targets that undergo SIEP reaction can be distinguished visually from non-specific spots at 1 nM concentration compared to 100 nM for target without SIEP amplification. However, when we plot the intensity of spots (background corrected mean intensity) generated from hybridized target with and without SIEP amplification, the LOD for both assay is the same (LOD is determined from identifying the concentration with signal intensity of zero targets plus three times the standard deviation). Although technically SIEP does not improve the LOD of DNA hybridization assay, visually SIEP improve the assay sensitivity by 100 fold. In addition, from our experience generating dose response curves, SIEP amplification produce a more consistent increase in signal intensities than without SIEP amplification as the target concentration increases.

We compared our result with the result published by Kim et al., (Kim et al. 2010) where they hybridized 18-mer target to a PNA probe and carry out AuNPs labeling and gold enhancement. They showed data with LOD of 10 pM and claimed that their assay is as sensitive as fluorescent labeled targets. In our hand, this result is not repeatable. The discrepancy between our data and their finding is probably due to variations in sample processing and assessment of the data (their data is 8-bit grayscale while our data is 16-bit grayscale, see methods). Another key step probably lies in the gold enhancement step as we often observed significant signal produced by PNA probe alone without target exposure, which is likely caused by the binding of the Au NP to the bases in the PNA (Gourishankar et al. 2004) and result in high level of "background" signal within the spot itself (not from the substrate) as shown in optical microscopy image. This high level background within a spot has prevented the assay to assess target hybridization at low concentrations (<1 nM).

Figure 8A:
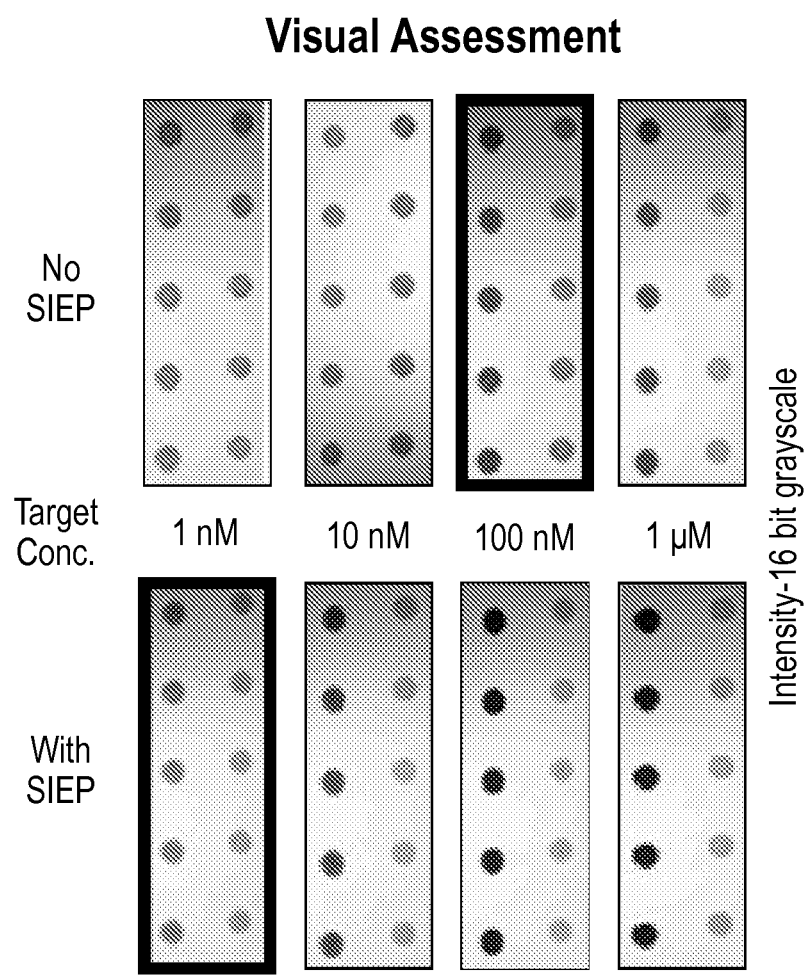
FIG. 8(a) shows a visual assessment with optical microscope images of metallized spots with fully complementary (left column) and non-specific (right column) PNA probes after exposure to a range of 22-mer DNA target. A sensitivity of 100 nM (highlighted) without SIEP amplification, while with SIEP, the sensitivity is 100 fold higher at 1 nM (highlighted).

FIG. 8(a) Visual assessment with optical microscope images of metallized spots with fully complementary (left column) and non-specific (right column) PNA probes after exposure to a range of 22-mer DNA target. A sensitivity of 100 nM (highlighted) without SIEP amplification, while with SIEP, the sensitivity is 100 fold higher at 1 nM (highlighted). FIG. 8(b) Dose response curve of hybridized 22-mer DNA target on PNA probe, with and without SIEP amplification

Example 26

Dose Response of RNA Target Hybridization

We demonstrate the use of SIEP colorimetric assay for the detection of hybridized RNA target by using PaP enzyme to replace the role of TdT enzyme. TdT is not efficient in initiating polymerization at the 3'-OH of an RNA, (Tjong et al. 2013) therefore a template independent RNA polymerase enzyme such as PaP is an ideal alternative. We have demonstrated that PaP can polymerize ATP from the 3'-OH of an RNA initiator and generate a long homopolyA. (Tjong et al. 2013) When this characteristic is used to grow long homopolyA from the RNA target bound to the immobilized probe, signal amplification can be attained through the increase in the net negative charge from the bound RNA target.

We assessed the SIEP amplification on the RNA target by hybridizing 28-mer RNA target onto the immobilized PNA probe. The hybridized target was then exposed to PaP reaction containing 0.1 mM ATP for 1 hr at 37° C., followed by incubation with positively charged AuNPs (~5 nm in diameter, CTAB modified) for 30 min. After rigorous rinsing, gold enhancement step was carried out for 5 min. The substrate with metallized DNA spots was then spun dry and imaged with a flatbed scanner for intensity analysis and an optical microscope for detailed morphology.

Figure 9A:
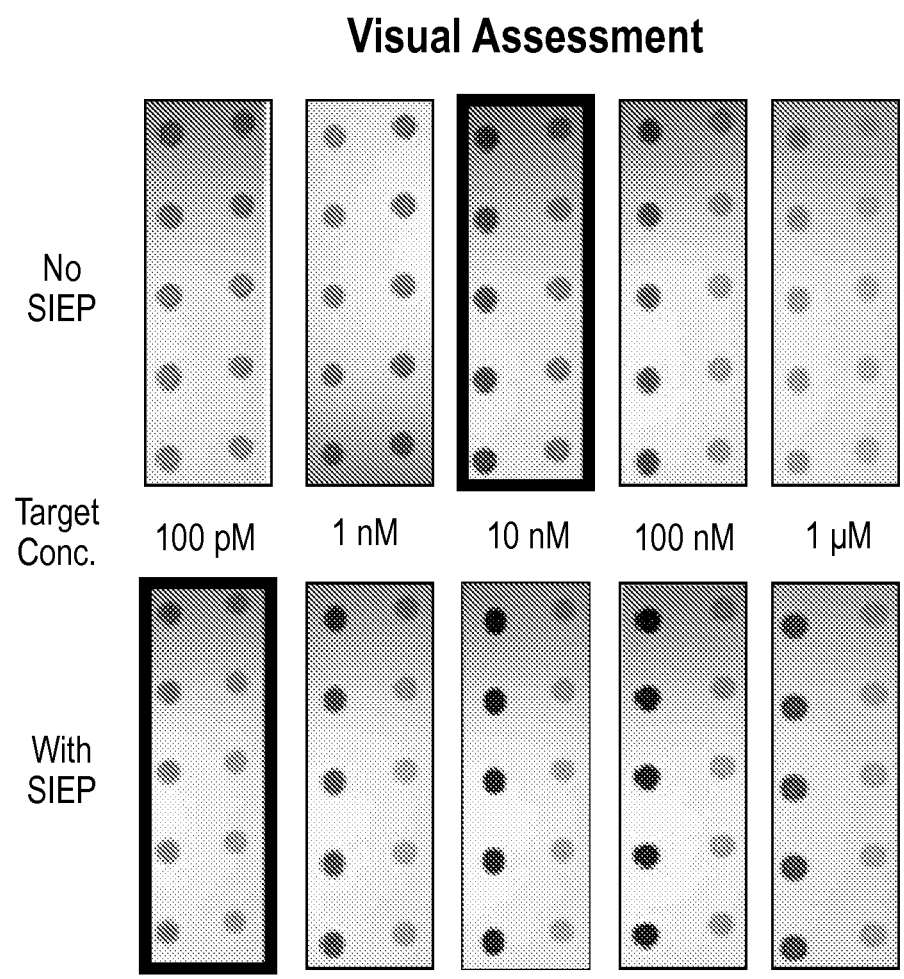
FIG. 9(a) shows visual assessment using optical microscope images of metallized spots with fully complementary (left column) and non-specific (right column) PNA probes.
Figure 10:
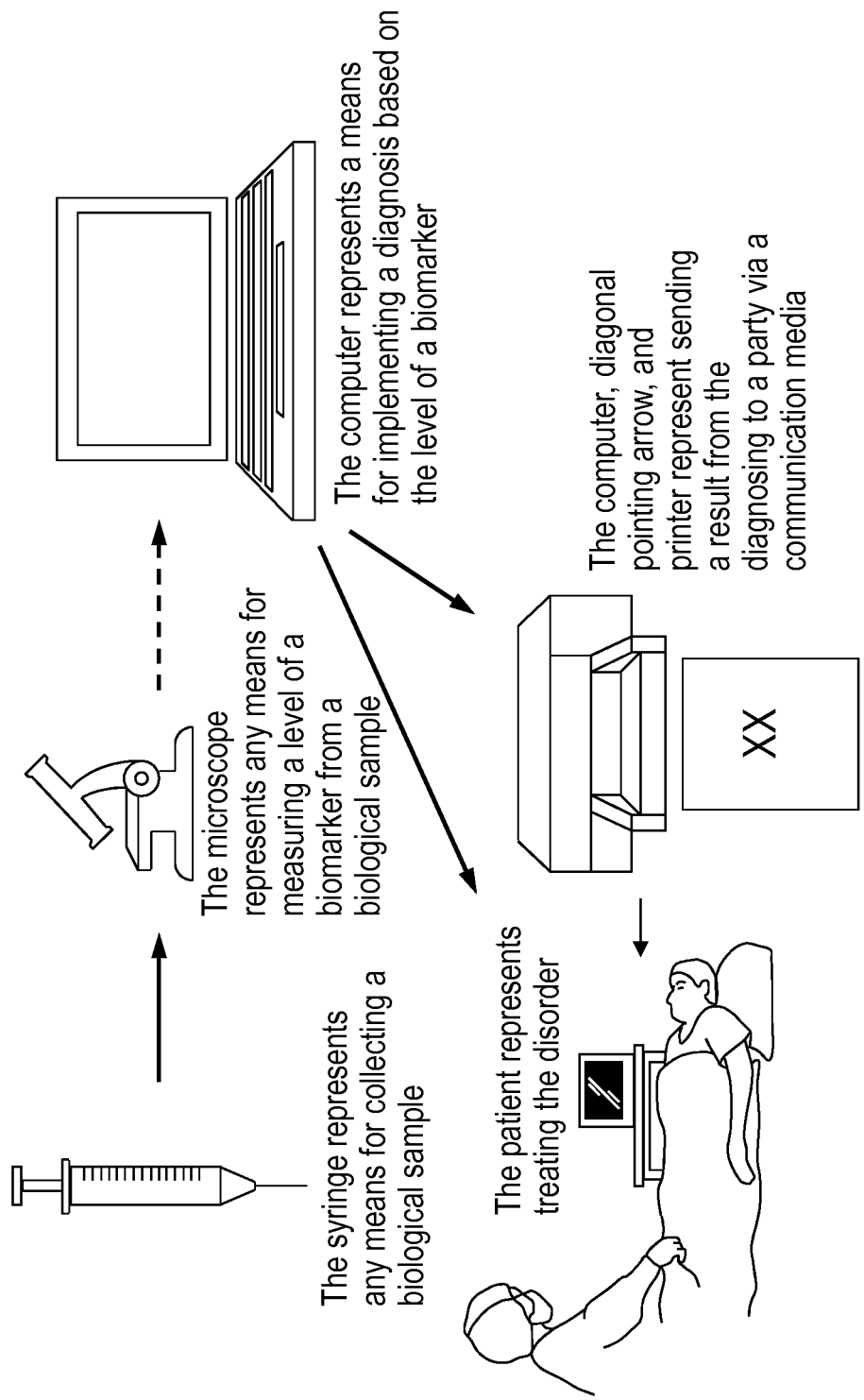
FIG. 10 illustrates an exemplary course of events related to a method of diagnosing a disease or condition.
Figure 11:
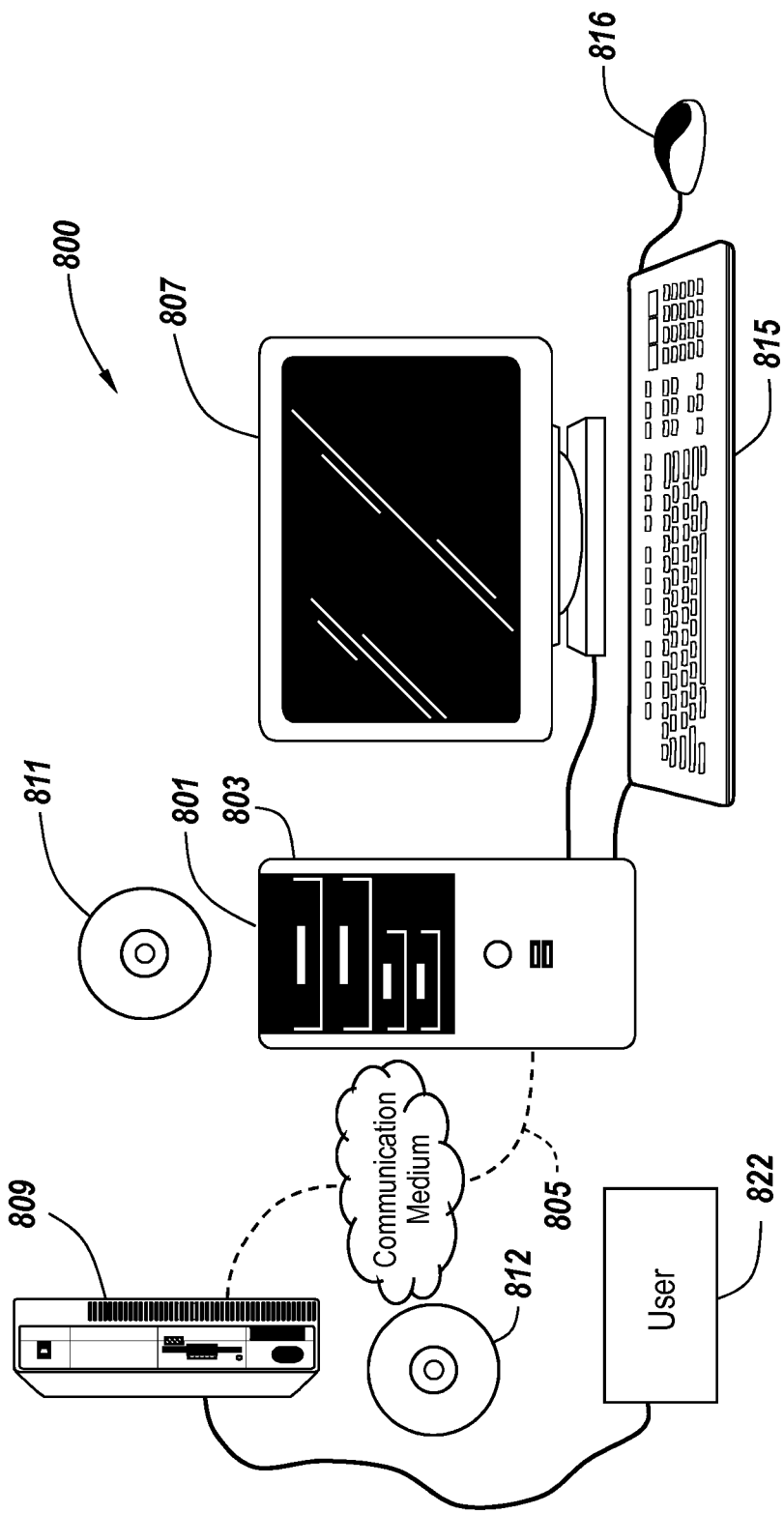
FIG. 11 depicts a computer system useful for displaying, storing, retrieving, or calculating diagnostic results from a level of one or more biomarkers; displaying, storing, retrieving, or calculating raw data from biomarker analysis; or displaying, storing, retrieving, or calculating any sample or subject information useful in the diagnostic methods disclosed herein. The computer system can include, for example, a CD or DVD rom, a key board, a mouse, a disk drive, a hard drive, a modem, a router, a processor, a microprocessor, and/or a screen.
Figure 12:
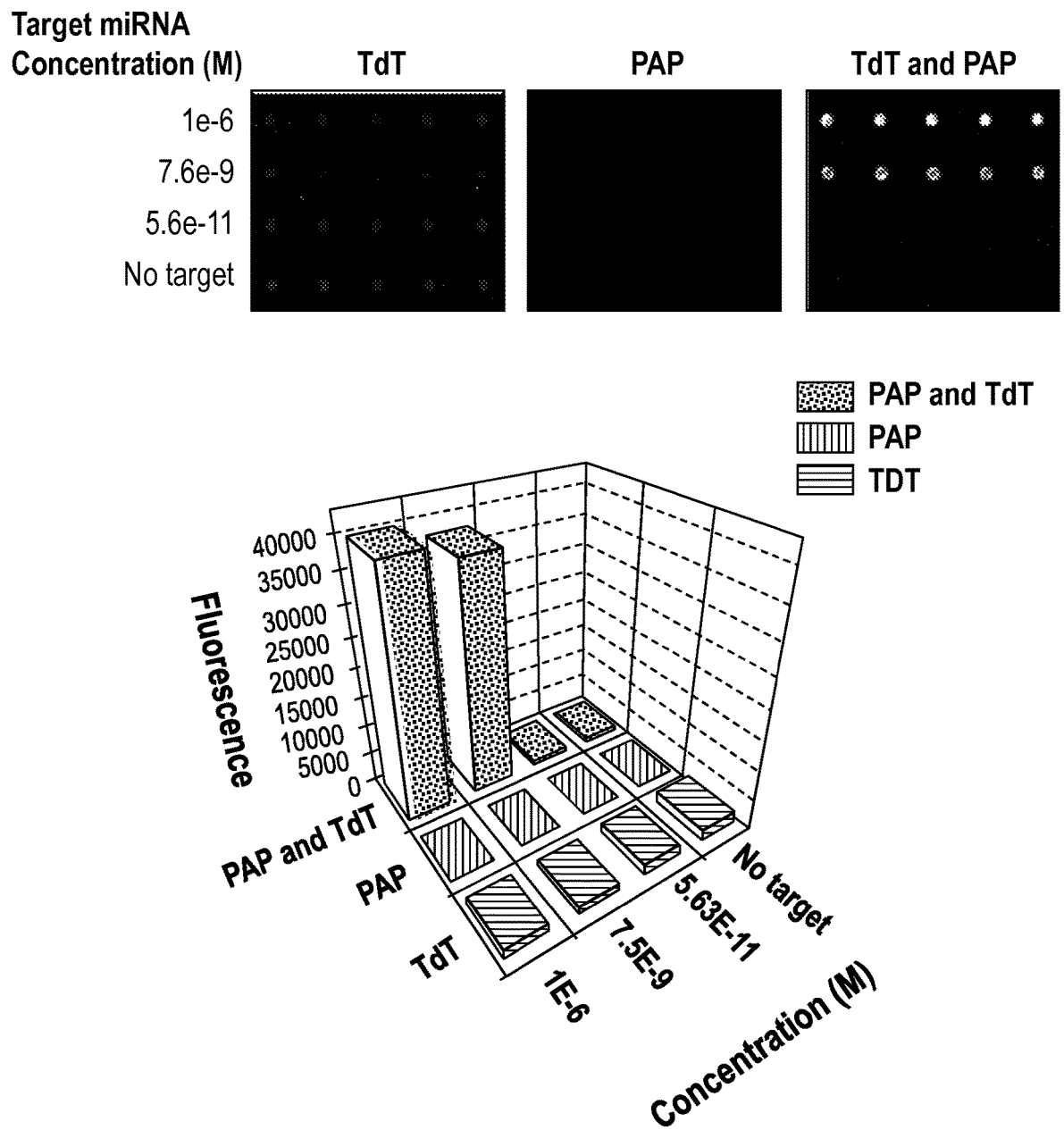
FIG. 12 depicts that better results are obtained with two enzymes. (a) Microspot images for three different cases (b) Background subtracted fluorescent intensities spots for various target concentrations and exposed to different enzymes.

We obtain 100 pM sensitivity and selectivity after SIEP amplification compared to 10 nM without SIEP, as shown by the optical microscope image in FIG. 9(a). This level of sensitivity is 10 fold more sensitive than the DNA detection. We believe the improvement in the sensitivity of RNA hybridization detection is due to higher affinity of PNA towards RNA than DNA. (Jensen et al. 1997) When we plot the background corrected intensities of spots generated from RNA hybridization (FIG. 9(b)), we obtain ~100 pM of LOD for SIEP amplified spots and ~1 nM LOD for hybridized RNA without amplification. The discrepancy in the sensitivity level is probably due to the technical definition of LOD. Nevertheless, visual assessment and intensity plot consistently show that SIEP amplification improves the detection sensitivity of RNA hybridization.

FIG. 9(a) Visual assessment using optical microscope images of metallized spots with fully complementary (left column) and non-specific (right column) PNA probes and FIG. 9(b) dose response curve of hybridized 28-mer RNA target on PNA probe, with and without STEP amplification. A sensitivity of 10 nM (highlighted) was determined visually without SIEP amplification, while with SIEP, the sensitivity is 100 fold higher at 10 nM (highlighted).

Overall, SIEP amplification on hybridized DNA and RNA target has improved the sensitivity of colorimetric detection by 100 fold, especially by comparing the metallization spot of specific probe with non-specific probe visually. In other words, SIEP amplification allows a more sensitive detection and a more robust assessment of positive hybridization events.

Example 27

Study Conclusions

We presented a scheme for STEP-based assay with colorimetric detection. In this scheme we utilized the ability of TdT and PaP to polymerize long DNA/RNA chains from the 3'-OH of a DNA/RNA initiator and the electrostatic interaction of positively charged AuNPs with the negatively charged DNA backbone. We demonstrated that in situ polymerization of DNA/RNA by SIEP, initiated from the hybridized DNA or RNA target produced long ssDNA/RNA chains that increases the net negative charge on the surface. This increase in negative charge attracted positively charged AuNPs, which then served as seeds for further metal deposition, allowing visual readout of target hybridization. We observed long homopolyadenine and AuNPs with 5 nm diameter and CTAB functionalization produced high metal deposition. Using SIEP amplification, visual readouts on hybridized DNA and RNA targets were obtained with sensitivities that were 100 fold higher than unamplified assay. Finally, this work has demonstrated the versatility of SIEP amplified assay for nucleic acid hybridization detection, extending signal detection from fluorescent to visual readout.

REFERENCES

Duggan, D. J.; Bittner, M.; Chen, Y.; Meltzer, P.; Trent, J. M. Nature genetics 1999, 21, 10-14.
Schulze, A.; Downward, J. Nature cell biology 2001, 3, E190-195.
Barrett, J. C.; Kawasaki, E. S. Drug discovery today 2003, 8, 134-141.
Liu, Y. T. Infectious disorders drug targets 2008, 8, 183-188.
Wang, D.; Coscoy, L.; Zylberberg, M.; Avila, P. C.; Boushey, H. A.; Ganem, D.; DeRisi, J. L. Proceedings of the National Academy of Sciences of the United States of America 2002, 99, 15687-15692.
Nelson, P. T.; Baldwin, D. A.; Scearce, L. M.; Oberholtzer, J. C.; Tobias, J. W.; Mourelatos, Z. Nat Methods 2004, 1, 155-161.
Thomson, J. M.; Parker, J.; Perou, C. M.; Hammond, S. M. Nat Methods 2004, 1, 47-53.
Shingara, J.; Keiger, K.; Shelton, J.; Laosinchai-Wolf, W.; Powers, P.; Conrad, R.; Brown, D.; Labourier, E. Rna-a Publication of the Rna Society 2005, 11, 1461-1470.
Wang, H.; Ach, R. A.; Curry, B. Rna-a Publication of the Rna Society 2007, 13, 151-159.
Vorwerk, S.; Ganter, K.; Cheng, Y.; Hoheisel, J.; Stahler, P. F.; Beier, M. New Biotechnol 2008, 25, 142-149.
Zhou, W. J.; Chen, Y.; Corn, R. M. Anal Chem 2011, 83, 3897-3902.
Freeman, W. M.; Walker, S. J.; Vrana, K. E. Biotechniques 1999, 26, 112-125.
Coller, J. A. In Batch Effects and Noise in Microarray Experiments: Sources and Solutions; Scherer, A., Ed.; John Wiley & Sons, Ltd, 2009, pp 5-17.
Wark, A. W.; Lee, H. J.; Corn, R. M. Angew Chem Int Edit 2008, 47, 644-652.
Naef, F.; Magnasco, M. O. Physical Review E 2003, 68, 0119061-0119064.
Hucknall, A.; Kim, D.-H.; Rangarajan, S.; Hill, R. T.; Reichert, W. M.; Chilkoti, A. Advanced Materials 2009, 21, 1968-1971.
Chow, D. C.; Lee, W. K.; Zauscher, S.; Chilkoti, A. Journal of the American Chemical Society 2005, 127, 14122-14123.
Tjong, V.; Yu, H.; Hucknall, A.; Rangarajan, S.; Chilkoti, A. Anal Chem 2011, 83, 5153-5159.
Fang, S. P.; Lee, H. J.; Wark, A. W.; Corn, R. M. Journal of the American Chemical Society 2006, 128, 14044-14046.
Hucknall, A.; Rangarajan, S.; Chilkoti, A. Advanced Materials 2009, 21, 2441-2446.
Paredes, E.; Evans, M.; Das, S. R. Methods 2011, 54, 251-259.
Proudnikov, D.; Mirzabekov, A. Nucleic acids research 1996, 24, 4535-4542.
Garnier, A.; Husken, D.; Weiler, J. Nucleosides, nucleotides & nucleic acids 2001, 20, 1181-1185.
Qin, P. Z.; Pyle, A. M. Methods 1999, 18, 60-70.
Paredes, E.; Das, S. R. Chembiochem: a European journal of chemical biology 2011, 12, 125-131.
Hilario, E. Mol Biotechnol 2004, 28, 77-80.
Igloi, G. L. Analytical Biochemistry 1996, 233, 124-129.
Cole, K.; Truong, V.; Barone, D.; McGall, G. Nucleic acids research 2004, 32, e86.
Lingner, J.; Keller, W. Nucleic acids research 1993, 21, 2917-2920.
Martin, G.; Keller, W. Rna-a Publication of the Rna Society 1998, 4, 226-230.
Rosemeyer, V.; Laubrock, A.; Seibl, R. Analytical Biochemistry 1995, 224, 446-449.
Jensen, K. K.; Orum, H.; Nielsen, P. E.; Norden, B. Biochemistry-Us 1997, 36, 5072-5077.
Lee, J. M.; Cho, H.; Jung, Y. Angew Chem Int Edit 2010, 49, 8662-8665.
Liang, R.-Q.; Li, W.; Li, Y.; Tan, C.-y.; Li, J.-X.; Jin, Y.-X.; Ruan, K.-C. Nucleic acids research 2005, 33,e17.
Hu, Z. L.; Zhang, A. X.; Storz, G.; Gottesman, S.; Leppla, S. H. Nucleic acids research 2006, 34.
Liu, W. T.; Guo, H.; Wu, J. H. Appl Environ Microbiol 2007, 73, 73-82.
Mehlmann, M.; Townsend, M. B.; Stears, R. L.; Kuchta, R. D.; Rowlen, K. L. Analytical Biochemistry 2005, 347, 316-323.
Squires, T. M.; Messinger, R. J.; Manalis, S. R. Nat Biotech 2008, 26, 417-426.
Sheehan, P. E.; Whitman, L. J. Nano Letters 2005, 5, 803-807.
Werner, A. Nucleic acids research 2010, 39, e17.
Cui, Z.-Q.; Zhang, Z.-P.; Zhang, X.-E.; Wen, J.-K.; Zhou, Y.-F.; Xie, W.-H. Nucleic acids research 2005, 33, 3245-3252.
Smith, D. E.; Perkins, T. T.; Chu, S. Macromolecules 1996, 29, 1372-1373.
Fixe, F.; Branz, H. M.; Louro, N.; Chu, V.; Prazeres, D. M.; Conde, J. P. Biosensors & bioelectronics 2004, 19, 1591-1597.
Bin, X.; Sargent, E. H.; Kelley, S. O. Anal Chem 2010, 82, 5928-5931.
U.S. patent application Ser. No. 10/783,054, filed Jan. 20, 2004.
U.S. Pat. App. Pub. No. 20060057180, published on Mar. 16, 2006.

U.S. patent application Ser. No. 12/405,300, filed on Mar. 17, 2009.

U.S. Pat. App. Pub. No. 20090247426, published on Oct. 1, 2009.

Bao, Y. P., Huber, M., Wei, T. F., Marla, S. S., Storhoff, J. J., Muller, U. R., 2005. SNP identification in unamplified human genomic DNA with gold nanoparticle probes. Nucleic acids research 33(2), e15.

Brandt, O., Feldner, J., Stephan, A., Schröder, M., Schnölzer, M., Arlinghaus, H. F., Hoheisel, J. D., Jacob, A., 2003. PNA microarrays for hybridization of unlabeled DNA samples. Nucleic acids research 31(19), e119.

Chow, D. C., Lee, W. K., Zauscher, S., Chilkoti, A., 2005. Enzymatic fabrication of DNA nanostructures: extension of a self-assembled oligonucleotide monolayer on gold arrays. Journal of the American Chemical Society 127 (41), 14122-14123.

Gourishankar, A., Shukla, S., Ganesh, K. N., Sastry, M., 2004. Isothermal titration calorimetry studies on the binding of DNA bases and PNA base monomers to gold nanoparticles. Journal of the American Chemical Society 126(41), 13186-13187.

He, L., Musick, M. D., Nicewarner, S. R., Salinas, F. G., Benkovic, S. J., Natan, M. J., Keating, C. D., 2000. Colloidal Au-Enhanced Surface Plasmon Resonance for Ultrasensitive Detection of DNA Hybridization. Journal of the American Chemical Society 122(38), 9071-9077.

Ho, H. A., Najari, A., Leclerc, M., 2008. Optical detection of DNA and proteins with cationic polythiophenes. Accounts of chemical research 41(2), 168-178.

Hucknall, A., Kim, D.-H., Rangarajan, S., Hill, R. T., Reichert, W. M., Chilkoti, A., 2009a. Simple Fabrication of Antibody Microarrays on Nonfouling Polymer Brushes with Femtomolar Sensitivity for Protein Analytes in Serum and Blood. Advanced Materials 21(19), 1968-1971.

Hucknall, A., Rangarajan, S., Chilkoti, A., 2009b. In Pursuit of Zero: Polymer Brushes that Resist the Adsorption of Proteins. Advanced Materials 21(23), 2441-2446.

Jensen, K. K., Orum, H., Nielsen, P. E., Norden, B., 1997. Kinetics for hybridization of peptide nucleic acids (PNA) with DNA and RNA studied with the BIAcore technique. Biochemistry-Us 36(16), 5072-5077.

Kanjanawarut, R., Su, X., 2009. Colorimetric detection of DNA using unmodified metallic nanoparticles and peptide nucleic acid probes. Analytical Chemistry 81(15), 6122-6129.

Kim, S. K., Cho, H., Jeong, J., Kwon, J. N., Jung, Y., Chung, B. H., 2010. Label-free and naked eye detection of PNA/DNA hybridization using enhancement of gold nanoparticles. Chem Commun (Camb) 46(19), 3315-3317.

Li, H., Rothberg, L., 2004. Colorimetric detection of DNA sequences based on electrostatic interactions with unmodified gold nanoparticles. Proceedings of the National Academy of Sciences of the United States of America 101(39), 14036-14039.

Liang, R. Q., Li, W., Li, Y., Tan, C. Y., Li, J. X., Jin, Y. X., Ruan, K. C., 2005. An oligonucleotide microarray for microRNA expression analysis based on labeling RNA with quantum dot and nanogold probe. Nucleic acids research 33(2), e17.

Liu, B., Bazan, G. C., 2005. Methods for strand-specific DNA detection with cationic conjugated polymers suitable for incorporation into DNA chips and microarrays. P Natl Acad Sci USA 102(3), 589-593.

Storhoff, J. J., Elghanian, R., Mucic, R. C., Mirkin, C. A., Letsinger, R. L., 1998. One-Pot Colorimetric Differentiation of Polynucleotides with Single Base Imperfections Using Gold Nanoparticle Probes. Journal of the American Chemical Society 120(9), 1959-1964.

Su, X., Teh, H. F., Lieu, X. H., Gao, Z. Q., 2007. Enzyme-based colorimetric detection of nucleic acids using peptide nucleic acid-immobilized microwell plates. Analytical Chemistry 79(18), 7192-7197.

Suzuki, T., Tanaka, M., Otani, S., Matsuura, S., Sakaguchi, Y., Nishimura, T., Ishizaka, A., Hasegawa, N., 2006. New rapid detection test with a combination of polymerase chain reaction and immunochromatographic assay for Mycobacterium tuberculosis complex. Diagnostic Microbiology and Infectious Disease 56(3), 275-280.

Taton, T. A., Mirkin, C. A., Letsinger, R. L., 2000. Scanometric DNA array detection with nanoparticle probes. Science 289(5485), 1757-1760.

Tjong, V., Yu, H., Hucknall, A., Chilkoti, A., 2013. Direct fluorescence detection of RNA on microarrays by surface-initiated enzymatic polymerization. Analytical Chemistry 85(1), 426-433.

Tjong, V., Yu, H., Hucknall, A., Rangarajan, S., Chilkoti, A., 2011. Amplified on-chip fluorescence detection of DNA hybridization by surface-initiated enzymatic polymerization. Analytical Chemistry 83(13), 5153-5159.

Wang, J., Rincon, O., Polsky, R., Dominguez, E., 2003. Electrochemical detection of DNA hybridization based on DNA-templated assembly of silver cluster. Electrochem Commun 5(1), 83-86.

Wilson, R., 2008. The use of gold nanoparticles in diagnostics and detection. Chem Soc Rev 37(9), 2028-2045.

Xia, F., Zuo, X., Yang, R., Xiao, Y., Kang, D., Vallee-Belisle, A., Gong, X., Yuen, J. D., Hsu, B. B., Heeger, A. J., Plaxco, K. W., 2010. Colorimetric detection of DNA, small molecules, proteins, and ions using unmodified gold nanoparticles and conjugated polyelectrolytes. Proceedings of the National Academy of Sciences of the United States of America 107(24), 10837-10841.

Anal. Chem. 2013, 85, 426-433.

U.S. Pat. No. 7,713,689.

U.S. Pat. No. 8,367,314.

Zheng, W. M., He, L., 2009. Label-Free, Real-Time Multiplexed DNA Detection Using Fluorescent Conjugated Polymers. Journal of the American Chemical Society 131(10), 3432-3433.

What is claimed is:

1. A method of detecting a target RNA from a biological sample, comprising the steps of:
   a) annealing the target RNA from the biological sample to one of a plurality of polynucleotide probes, thereby forming a complex comprising the one of the polynucleotide probes and the target RNA, wherein the plurality of polynucleotide probes are DNA probes;
   b) extending the 3' end of the target RNA in the complex with at least one deoxyadenosine triphosphate using a poly(A) polymerase, thereby forming an RNA-DNA hybrid;
   c) extending the RNA-DNA hybrid with at least one deoxyribonucleotide triphosphate using a DNA polymerase, thereby forming an extended RNA-DNA hybrid, wherein the DNA polymerase is a terminal deoxynucleotidyl transferase; and
   d) detecting the target RNA from the biological sample by detecting the extended RNA-DNA hybrid.

2. The method of claim 1, wherein the at least one deoxyribonucleotide triphosphate in step c) is labeled.

3. The method of claim 2, wherein the label is a fluorescent label.

4. The method of claim 1, wherein the target RNA is a mammalian RNA, an eukaryotic RNA, a human RNA, or a fragment thereof.

5. The method of claim 1, wherein the target RNA is associated with a disease or condition selected from the group consisting of: tuberculosis, *Chlamydia*, gonorrhea, syphilis, mumps, measles, cholera, typhoid fever, rheumatic fever, cancer, stroke, ischemic disease, cardiovascular disease, Lyme disease, rabies, influenza, Ebola, pregnancy, a fungal infection, a bacterial infection, polio, small pox, diabetes, diabetes type I, diabetes type II, a viral infection, and an autoimmune disease, and any combination thereof.

6. The method of claim 5, wherein the viral infection is associated with human immunodeficiency virus (HIV), herpes simplex virus (HSV), herpes simplex virus-1 (HSV-1), herpes simplex virus-2 (HSV-2), human papillomavirus (HPV), human papillomavirus-16 (HPV-16), human papillomavirus-18 (HPV-18), hepatitis C virus (HCV), hepatitis B virus (HBV), hepatitis A virus (HVA), cytomegalovirus, and any combination thereof.

7. The method of claim 5, wherein the bacterial infection is associated with Methicillin-resistant *Staphylococcus aureus* (MRSA).

8. The method of claim 1, wherein the target RNA is not labeled before step (b).

9. The method of claim 1, wherein the plurality of polynucleotide probes is directly associated with a solid support, a layer or a surface thereof.

10. The method of claim 9, wherein the plurality of polynucleotide probes is associated with the solid support, the layer or the surface thereof covalently.

11. The method of claim 1, further comprising, before step a), printing the plurality of polynucleotide probes onto a solid support.

12. The method of claim 11, wherein the solid support comprises a substrate and a non-fouling, bottle-brush polymer layer.

13. The method of claim 12, wherein the non-fouling, bottle-brush polymer layer comprises a copolymer.

14. The method of claim 12, wherein the non-fouling, bottle-brush polymer layer comprises poly(oligo(ethylene glycol) methacrylate.

15. The method of claim 12, wherein the solid support further comprises a linking layer, and wherein the linking layer is between the substrate and the non-fouling, bottle-brush polymer layer.

16. The method of claim 15, wherein the non-fouling, bottle-brush polymer layer is covalently connected to the linking layer.

17. The method of claim 15, wherein the linking layer is a polymer.

18. The method of claim 15, wherein the linking layer is a copolymer.

19. The method of claim 1, wherein the method is conducted using an array, and wherein the plurality of polynucleotide probes is located on the array.

20. The method of claim 19, wherein the array is a microarray.

21. The method of claim 1, wherein at least one of steps a), b), c), and/or d) is conducted isothermally.

22. The method of claim 1, wherein the poly(A) polymerase is a yeast poly(A) polymerase.

23. The method of claim 1, wherein the DNA polymerase recognizes the 3' OH group of the 3' terminal deoxyadenosine of the target RNA in the RNA-DNA hybrid of step b), wherein the 3' terminal deoxyadenosine is extended by the poly(A) polymerase.

24. The method of claim 1, further comprising associating the complex from step a) with a solid support.

25. The method of claim 1, further comprising associating the RNA-DNA hybrid from step b) with a solid support.

26. The method of claim 1, further comprising associating the extended RNA-DNA hybrid from step c) with a solid support.

27. The method of claim 1, wherein said detecting the extended RNA-DNA hybrid is by a fluorescence detection method.

28. The method of claim 27, further comprising determining the amount of the target RNA.

29. The method of claim 1, wherein steps b) and c) are conducted sequentially.

30. The method of claim 1, wherein steps b) and c) are conducted together.

31. The method of claim 1, wherein the one of the polynucleotide probes is blocked with a blocking group at its 5' end.

32. The method of claim 31, wherein the blocking group is an acyl group.

33. The method of claim 31, wherein the blocking group is an acetyl group.

34. The method of claim 1, wherein the one of the polynucleotide probes specifically hybridizes to the target RNA.

35. The method of claim 1, wherein the annealing step is conducted at about 42° C.

36. The method of claim 1, further comprising dephosphorylating the target RNA in the complex.

37. The method of claim 36, wherein the target RNA of the complex is dephosphorylated with a base.

38. The method of claim 37, wherein the base is one or more of an organic or inorganic hydroxide selected from the group consisting of ammonium hydroxide, lithium hydroxide, potassium hydroxide, sodium hydroxide, magnesium hydroxide, cesium hydroxide, and calcium hydroxide.

39. The method of claim 36, wherein the target RNA of the complex is dephosphorylated with an enzyme.

40. The method of claim 39, wherein the enzyme is a phosphatase.

41. The method of claim 1, wherein the biological sample is subjected to lysing conditions prior to step a).

42. The method of claim 1, wherein the target RNA of the complex contains an overhanging 3' end that is not annealed to the polynucleotide probe.

43. The method of claim 1, wherein the plurality of polynucleotide probes comprises at least two different polynucleotide probes, wherein the at least two different polynucleotide probes specifically hybridize to at least two different target RNAs in the biological sample.

44. The method of claim 1, wherein the biological sample comprises blood, plasma, lymph, saliva, mucus, cerebral spinal fluid, synovial fluid, stomach fluid, intestinal fluid, cytoplasmic fluid, a biopsy, a tissue biopsy, a viral sample, a bacterial sample, a human sample, a diseased human sample, an animal sample, and a disease animal sample.

* * * * *